(12) United States Patent
Moser

(10) Patent No.: US 8,293,472 B2
(45) Date of Patent: Oct. 23, 2012

(54) METHODS FOR DETECTION AND TYPING OF NUCLEIC ACIDS

(75) Inventor: Michael James Moser, Madison, WI (US)

(73) Assignee: Luminex Corporation, Austin, TX (US)

( * ) Notice: Subject to any disclaimer, the term of this patent is extended or adjusted under 35 U.S.C. 154(b) by 432 days.

(21) Appl. No.: 11/447,734

(22) Filed: Jun. 6, 2006

(65) Prior Publication Data

US 2010/0221702 A1  Sep. 2, 2010

Related U.S. Application Data

(60) Provisional application No. 60/688,409, filed on Jun. 7, 2005.

(51) Int. Cl.
*C12Q 1/68* (2006.01)
*C12P 19/34* (2006.01)

(52) U.S. Cl. .......................... 435/6.12; 435/6.1; 435/6.11

(58) Field of Classification Search ........................ None
See application file for complete search history.

(56) References Cited

U.S. PATENT DOCUMENTS

| | | | |
|---|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 4,996,143 A | 2/1991 | Heller et al. |
| 5,126,439 A | 6/1992 | Rappaport |
| 5,177,064 A | 1/1993 | Bodor |
| 5,210,015 A | 5/1993 | Gelfand et al. |
| 5,412,088 A | 5/1995 | Jones et al. |
| 5,432,272 A | 7/1995 | Benner |
| 5,470,974 A | 11/1995 | Summerton et al. |
| 5,604,097 A | 2/1997 | Brenner |
| 5,605,794 A | 2/1997 | Rust et al. |
| 5,679,524 A | 10/1997 | Nikiforov et al. |
| 5,681,702 A | 10/1997 | Collins et al. |
| 5,705,621 A | 1/1998 | Ravikumar |
| 5,736,330 A | 4/1998 | Fulton |
| 5,843,669 A | 12/1998 | Kaiser et al. |

(Continued)

FOREIGN PATENT DOCUMENTS

EP  0 382 433 B1  8/1990

(Continued)

OTHER PUBLICATIONS

O'Meara et al., "Monitoring Resistance to Human Immunodeficiency Virus Type 1 Protease Inhibitors by Pyrosequencing," Journal of Clinical Microbiology, Feb. 2001, vol. 39, No. 2, pp. 464-473.*

(Continued)

*Primary Examiner* — Young J Kim
(74) *Attorney, Agent, or Firm* — Fulbright & Jaworski L.L.P.

(57) ABSTRACT

Disclosed are methods for identifying and characterizing polynucleotide sequences in a sample which may include a heterogeneous sample. Some of the methods are directed to the identification and characterization of a virus in a sample, which may include HIV capable of cause AIDS or AIDS-like symptoms. The virus may be HIV-1, and may also include drug resistant mutations. The methods may include reacting a mixture that includes, in addition to nucleic acid isolated from the sample, at least one oligonucleotide capable of specifically hybridizing to HIV nucleic acid where the oligonucleotide includes at least one non-natural base. In addition, the methods may include detection of one or more mutations in HIV nucleic acid that are associated with drug resistance.

24 Claims, 8 Drawing Sheets

U.S. PATENT DOCUMENTS

| | | | |
|---|---|---|---|
| 5,846,717 A | 12/1998 | Brow et al. | |
| 5,856,092 A | 1/1999 | Dale et al. | |
| 5,928,869 A | 7/1999 | Nadeau et al. | |
| 5,958,784 A | 9/1999 | Benner | |
| 5,965,364 A | 10/1999 | Benner | |
| 6,001,983 A | 12/1999 | Benner | |
| 6,007,984 A | 12/1999 | Wang et al. | |
| 6,037,120 A | 3/2000 | Benner | |
| 6,046,807 A | 4/2000 | Chandler | |
| 6,054,270 A | 4/2000 | Southern | |
| 6,057,107 A | 5/2000 | Fulton | |
| 6,140,496 A | 10/2000 | Benner | |
| 6,200,757 B1 | 3/2001 | Kurn et al. | |
| 6,232,462 B1 | 5/2001 | Collins et al. | |
| 6,287,766 B1 | 9/2001 | Nolan et al. | |
| 6,294,336 B1 | 9/2001 | Boyce-Jacino et al. | |
| 6,444,798 B1 | 9/2002 | Benner | |
| 6,548,250 B1 | 4/2003 | Sorge | |
| 6,617,106 B1 | 9/2003 | Benner | |
| 6,627,456 B1 | 9/2003 | Benner | |
| 6,833,257 B2 | 12/2004 | Lee et al. | |
| 6,977,161 B2 | 12/2005 | Grenier et al. | |
| 7,498,136 B2 * | 3/2009 | Johnson | 435/6.12 |
| 2002/0055104 A1 | 5/2002 | Michelotti | |
| 2002/0132221 A1 | 9/2002 | Chee et al. | |
| 2002/0150900 A1 | 10/2002 | Marshall et al. | |
| 2003/0194705 A1 | 10/2003 | Schroth | |
| 2004/0106108 A1 | 6/2004 | Grenier et al. | |
| 2005/0014163 A1 | 1/2005 | Dong et al. | |
| 2005/0084894 A1 | 4/2005 | Brow et al. | |
| 2006/0078936 A1 | 4/2006 | Grenier et al. | |

FOREIGN PATENT DOCUMENTS

| | | |
|---|---|---|
| EP | 0 416 817 B1 | 3/1991 |
| EP | 0 742 287 A2 | 11/1996 |
| EP | 0 915 174 A1 | 5/1999 |
| EP | 1400601 A1 * | 3/2004 |
| WO | WO 90/06042 A2 | 6/1990 |
| WO | WO 92/11389 A1 | 7/1992 |
| WO | WO 92/20702 A1 | 11/1992 |
| WO | WO 94/21820 A1 | 9/1994 |
| WO | WO 96/31622 A1 | 10/1996 |
| WO | WO 97/46711 A1 | 12/1997 |
| WO | WO 98/14610 A2 | 4/1998 |
| WO | WO 01/90417 A2 | 11/2001 |
| WO | WO 02/33126 | 4/2002 |
| WO | WO 03/066897 A2 * | 8/2003 |

OTHER PUBLICATIONS

Myakishev et al., "High-Throughput SNP Genotyping by Allele-Specific PCR with Universal Energy-Transfer-Labeled Primers," Genome Research, 2001, vol. 11, pp. 163-169.*

Jordan et al., "Genome complexity reduction for SNP genotyping analysis," PNAS, Mar. 2002, vol. 99, No. 5, pp. 2942-2947.*

Biggins et al., "A continuous assay for DNA cleavage: The application of "break lights" to enediynes, iron-dependent agents, and nucleases", PNAS, vol. 97, No. 25, Dec. 5, 2000 (pp. 13537-13542).

Cobianchi et al., "Enzymes for Modifying and Labeling DNA and RNA", Methods in Enzymology, vol. 152, Copyright © 1987 by Academic Press, Inc., (pp. 94-110).

Hall et al., "Sensitive detection of DNA polymorphisms by the serial invasive signal amplification reaction", PNAS, vol. 97, No. 15, Jul. 18, 2000 (pp. 8272-8277).

Horlacher et al., "Recognition by viral and cellular DNA polymerases of nucleosides bearing bases with nonstandard hydrogen bonding patterns", Proc. Natl. Acad. Sci., vol. 92, Jul. 1995 (pp. 6329-6333).

Johnson et al., "A third base pair for the polymerase chain reaction: inserting isoC and isoG", Nucleic Acids Research, vol. 32, No. 6, 2004, (pp. 1937-1941).

Jurczyk et al., "Synthesis of 2'-Deoxyisoguanosine 5'-Triphosphate and 2'-Deoxy-5-methylisocytidine 5'-Triphosphate", Helvetica Chimica Acta, vol. 82, 1999 (pp. 1005-1015).

Lutz, Michael J. et al., "Differential discrimination of DNA polymerases for variants of the non-standard nucleobase pair between xanthosine and 2,4-diaminopyrimidine, two components of an expanded genetic alphabet", Nucleic Acids Research, vol. 24, No. 7, 1996 (pp. 1308-1313).

Lutz, Stefan et al., "An in vitro screening technique for DNA polymerases that can incorporate modified nucleotides. Pseudothymidine as a substrate for thermostable polymerases", Nucleic Acids Research, vol. 27, No. 13, 1999 (pp. 2792-2798).

Moser et al., "Quantifying Mixed Populations of Drug-Resistant Human Immunodeficiency Virus type 1", Antimicrobial Agents and Chemotherapy, vol. 49, No. 8, Aug. 2005 (pp. 3334-3340).

Moser et al., "Enzymatic repair of an expanded genetic information system", Nucleic Acids Research, vol. 31, No. 27, 2003 (pp. 5048-5053).

Newton et al., "The production of PCR products with 5' single-stranded tails using primers that incorporate novel phosphoramidite intermediates", Nucleic Acids Research, vol. 21, No. 5, 1993 (pp. 1155-1162).

Piccirilli et al., "Enzymatic incorporation of a new base pair into DNA and RNA extends the genetic alphabet", Reprinted from Nature, vol. 343, No. 6253, Jan. 4, 1990 (pp. 33-37).

Randerath et al., "$^3$H and $^{32}$P Derivative Methods for Base Composition and Sequence Analysis of RNA", Methods in Enzymology, vol. 65, Copyright © 1980 by Academic Press, Inc., (pp. 638-681).

Sepiol et al., "Tautomerism of Isoguanosine and Solvent-Induced Keto-Enol Equilibrium", Z. Naturforsch, 1976 (pp. 361-370).

Sismour et al., "The use of thymidine analogs to improve the replication of an extra DNA base pair: a synthetic biological system", Nucleic Acids Research, vol. 33, No. 17, 2005 (pp. 5640-5646).

Sismour et al., "PCR amplification of DNA containing non-standard base pairs by variants of reverse transcriptase from Human Immunodeficiency Virus-1", Nucleic Acids Research, vol. 32, No. 2, 2004 (pp. 728-735).

Switzer et al., "Enzymatic Recognition of the Base Pair between Isocytidine and Isoguanosine", Biochemistry, vol. 32, No. 39, 1993 (pp. 10489-10496).

Tabrizi et al., "Evaluation of real time polymerase chain reaction assays for confirmation of Neisseria gonorrhoeae in clinical samples. tested positive in the Roche Cobas Amplicor assay", Sex Transm Infect, vol. 80, 2004 (pp. 68-71).

Tor et al., "Site-Specific Enzymatic Incorporation of an Unnatural Base, $N^6$-(6-Aminohexyl)isoguanosine, into RNA", J. Am. Chem. Soc., vol. 115, No. 11, 1993 (pp. 4461-4467).

Von Krosigk et al., "pH-Independent Triple Helix Formation by an Oligonucleotide Containing a Pyrazine Donor-Donor-Acceptor Base", J. Am. Chem. Soc., vol. 117, No. 19, 1995 (pp. 5361-5362).

Walker et al., "Isothermal in vitro amplification of DNA by a restriction enzyme/DNA polymerase system", Proc. Natl. Acad. Sci., vol. 89, Jan. 1992 (pp. 392-396).

Zubay, "A Case for an Additional RNA Base Pair in Early Evolution", Reprint from: The Roots of Modern Biochemistry, © 1988 Walter de Gruyter & Co., Berlin, New York (4 pp.).

Cleland et al., "Evolution of Zidovudine Resistance-Associated Genotypes in Human Immunodeficiency Virus Type 1-Infected Patients", Journal of Acquired Immune Deficiency Syndromes and Human Retrovirology, vol. 12, No. 1, 1996 (pp. 6-18).

Cornelissen et al., "pol Gene Diversity of Five Human Immunodeficiency Virus Type 1 Subtypes: Evidence for Naturally Occuring Mutations That Contribute to Drug Resistance, Limited Recombination Patterns, and Common Ancestry for Subtypes B and D", Journal of Virology, vol. 71, No. 9, Sep. 1997 (pp. 6348-6358).

Eastman et al., "Comparison of Selective Polymerase Chain Reaction Primers and Differential Probe Hybridization of Polymerase Chain Reaction Products for Determination of Relative Amounts of Codon 215 Mutant and Wild-Type HIV-1 Populations", Journal of Acquired Immune Deficiency Syndromes and Human Retrovirology, vol. 9, No. 3, Jul. 1, 1995 (pp. 264-273).

Fontenot et al., "PCR Amplification of HIV-1 Proteinase Sequences Directly from Lab Isolates Allows Determination of Five Conserved Domains", Virology, vol. 190, 1992 (pp. 1-10).

Frenkel et al., "Specific, Sensitive, and Rapid Assay for Human Immunodeficiency Virus type 1 pol Mutations Associated with Resistance to Zidovudine and Didanosine", Journal of Clinical Microbiology, vol. 33, No. 2, Feb. 1995 (pp. 342-347).

Gingeras et al., "Use of Self-Sustained Sequence Replication Amplification Reaction to Analyze and Detect Mutations in Zidovudine-Resistant Human Immunodeficiency Virus", *The Journal of Infectious Diseases*, vol. 164, No. 6, Dec. 1991 (pp. 1066-1074).

Ives et al., "Emergence of resistant variants of HIV in vivo during monotherapy with the proteinase inhibitor saquinavir", *Journal of Antimicrobial Chemotherapy*, vol. 39, 1997 (pp. 771-779).

Johnson et al., "Update of the Drug Resistance Mutations in HIV-1: Fall 2005", *Topics in HIV Medicine*, Special Contribution—Drug Resistance Mutations in HIV-1, vol. 13, Issue 4, Oct./Nov. 2005 (pp. 125-131).

Leal et al., "Rate of development of mutation at codon 215 of HIV-1 reverse transcriptase and its predictive factors at the time of initiation of zidovudine therapy", *European Journal of Clinical Investigation*, vol. 26, 1996, (pp. 476-480).

McCutchan, "Understanding the genetic diversity of HIV-1", *AIDS*, vol. 14, Supplement 3, 2000 (pp. S31-S44).

McMinn et al., "Efforts toward Expansion of the Genetic Alphabet: DNA Polymerase Recognition of a Highly Stable, Self-Pairing Hydrophobic Base", *J. Am. Chem. Soc.*, vol. 121, No. 49, 1999 (pp. 11585-11586).

Najera, "Natural Occurrence of Drug Resistance Mutations in the Reverse Transcriptase of Human Immunodeficiency Virus Type 1 Isolates", *AIDS Research and Human Retroviruses*, vol. 10, No. 11, (pp. 1479-1488).

Ren et al., "Naphthalene, Phenanthrene, and Pyrene as DNA Base Analogues: Synthesis, Structure, and Fluorescence in DNA", *J. Am. Chem. Soc.*, vol. 118, No. 33, 1996 (pp. 7671-7678).

Richman et al., "Detection of Mutations Associated with Zidovudine Resistance in Human Immunodeficiency Virus by Use of the Polymerase Chain Reaction", *The Journal of Infectious Diseases*, vol. 164, No. 6, Dec. 1991 (pp. 1075-1081).

Robertson et al., "HIV-1 Nomenclature Proposal", *Human Retroviruses and AIDS, A Complication and Analysis of Nucleic and Amino Acid Sequences*, 1999, (pp. 492-505).

Schinazi et al., "Characterization of Human Immunodeficiency Viruses Resistant to Oxathiolane-Cytosine Nucleosides", *Antimicrobial Agents and Chemotherapy*, vol. 37, No. 4, Apr. 1993 (pp. 875-881).

Schmit et al., "Resistance-related mutations in the HIV-1 protease gene of patients treated for 1 year with the protease inhibitor ritonavir (ABT-538)", *AIDS*, vol. 10, No. 9, Aug. 1996 (pp. 995-999).

Shirasaka et al., "Emergence of human immunodeficiency virus type 1 variants with resistance to multiple dideoxynucleosides in patients receiving therapy with dideoxynucleosides", *Proc. Natl. Acad. Sci. USA*, vol. 92, Mar. 1995 (pp. 2398-2402).

Vasudevachari et al., "Emergence of Protease Inhibitor Resistance Mutations in Human Immunodeficiency Virus Type 1 Isolates from Patients and Rapid Screening Procedure for Their Detection", *Antimicrobial Agents and Chemotherapy*, vol. 40, No. 11, Nov. 1996 (pp. 2535-2541).

Wain-Hobson, "Is Antigenic Variation of HIV Important for AIDS and What Might Be Expected in the Future?", *The Evolutionary Biology of Viruses*, 1994 (pp. 185-209).

Winslow et al., "Selection conditions affect the evolution of specific mutations in the reverse transcriptase gene associated with resistance to DMP 266", *AIDS*, vol. 10, No. 11, Sep. 1996 (pp. 1205-1209).

Klevytska, Alexandra M. et al., "Analysis of length variation in the V1-V2 region of env in nonsubtype B HIV type 1 from Uganda." *Aids Research and Human Retroviruses*, vol. 18, No. 11, pp. 791-796, XP002416430, Jul. 20, 2002.

Sherrill, C.B. et al., "Nucleic acid analysis using an expanded genetic alphabet to quench fluorescence." *Journal of the American Chemical Society*, vol. 126, No. 14, pp. 4550-4556, XP002314862, Apr. 14, 2004.

Examination Report received for European Appln. No. 06772280.1 dated Apr. 19, 2010.

Gerard et al., "Fluorometric detection of HIV-1 genome through use of an internal control, inosine-substituted primers, and microtiter plate format," Clinical Chemistry, vol. 42, No. 5, May 1996, pp. 696-703.

Guo et al., "Enhanced Discrimination of Single Nucleotide Polymorphisms by Artificial Mismatch Hybridization," Nature Biotechnology, vol. 15, Apr. 1997, pp. 331-335.

Office Communication, issued in European Patent Application No. 06772280.1, mailed on Oct. 14, 2011.

Extended European Search Report issued in European Patent Application No. 12 16 5552.6, dated Jul. 12, 2012.

Guttman et al., "Multiple infections of ixodes scapularis ticks by *Borrelia burgodorferi* as revealed by single-strand conformation polymorphism analysis," *J. Clin Microbio.*, 34(3):652-656, 1996.

Office Communication issued in European Patent Application No. 06 772 280.1, dated Jul. 30, 2012.

\* cited by examiner

FIGURE 1

SEQ ID NO:1

FFREDLAFPQGKAREFSSEQTRANSPTRRELQVWGRDNNSLSEAGADRQGTVSFSFP

QITLWQRPLVTIKIGGQLKEALLDTGADDTVLEEMNLPGRWKPKMIGGIGGFIKVGQ

YDQILIEICGHKAIGTVLVGPTPVNIIGRNLLTQIGCTLNFPISPIETVPVKLKPGM

DGPKVKQWPLTEEKIKALVEICTEMEKEGKISKIGPENPYNTPVFAIKKKDSTKWRK

LVDFRELNKRTQDFWEVQLGIPHPAGLKQKKSVTVLDVGDAYFSVPLDKDFRKYTAF

TIPSINNETPGIRYQYNVLPQGWKGSPAIFQCSMTKILEPFRKQNPDIVIYQYMDDL

YVGSDLEIGQHRTKIEELRQHLLRWGFTTPDKKHQKEPPFLWMGYELHPDKWTVQPI

VLPEKDSWTVNDIQKLVGKLNWASQIYAGIKVRQLCKLLRGTKALTEVVPLTEEAEL

ELAENREILKEPVHGVYYDPSKDLIAEIQKQGQGQWTYQIYQEPFKNLKTGKYARMK

GAHTNDVKQLTEAVQKIATESIVIWGKTPKFKLPIQKETWEAWWTEYWQATWIPEWE

FVNTPPLVKLWYQLEKEPIIGAETFYVDGAANRETKLGKAGYVTDRGRQKVVPLTDT

TNQKTELQAIHLALQDSGLEVNIVTDSQYALGIIQAQPDKSESELVSQIIEQLIKKE

KVYLAWVPAHKGIGGNEQVDGLVSAGIRKVLFLDGIDKAQEEHEKYHSNWRAMASDF

NLPPVVAKEIVASCDKCQLKGEAMHGQVDCSPGIWQLDCTHLEGKVILVAVHVASGY

IEAEVIPAETGQETAYFLLKLAGRWPVKTVHTDNGSNFTSTTVKAACWWAGIKQEFG

IPYNPQSQGVIESMNKELKKIIGQVRDQAEHLKTAVQMAVFIHNFKRKGGIGGYSAG

ERIVDIIATDIQTKELQKQITKIQNFRVYYRDSRDPVWKGPAKLLWKGEGAVVIQDN

SDIKVVPRRKAKIIRDYGKQMAGDDCVASRQDED

FIGURE 3A
A1
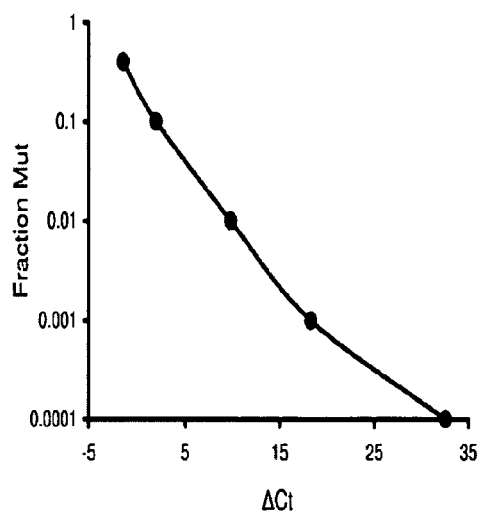
A2
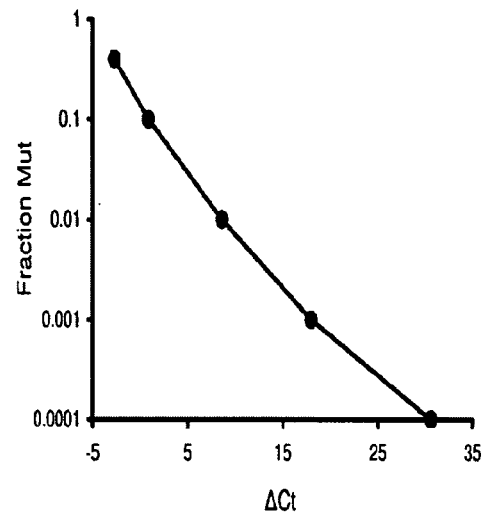
B1
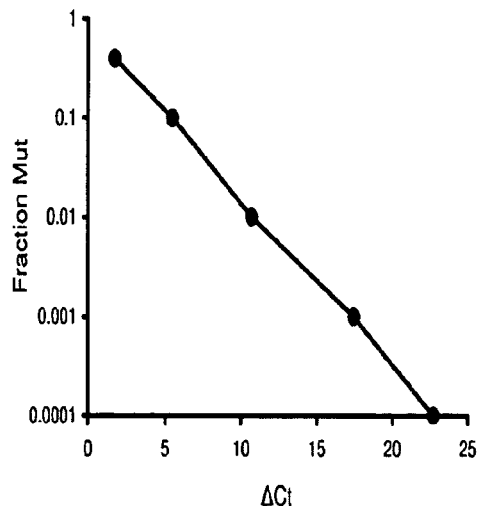
B2
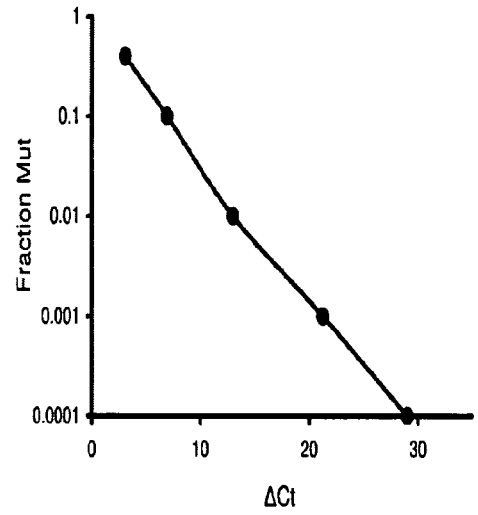

FIGURE 3B
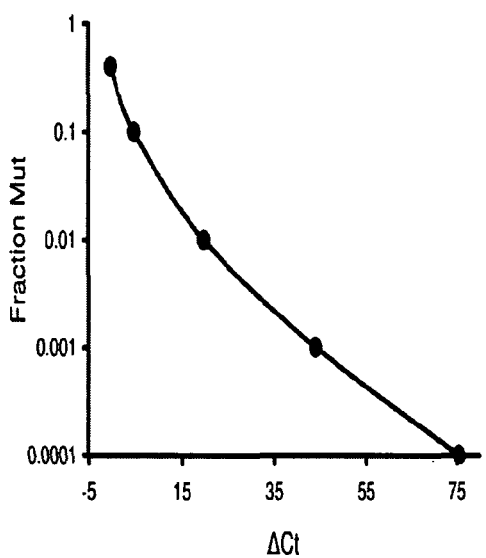
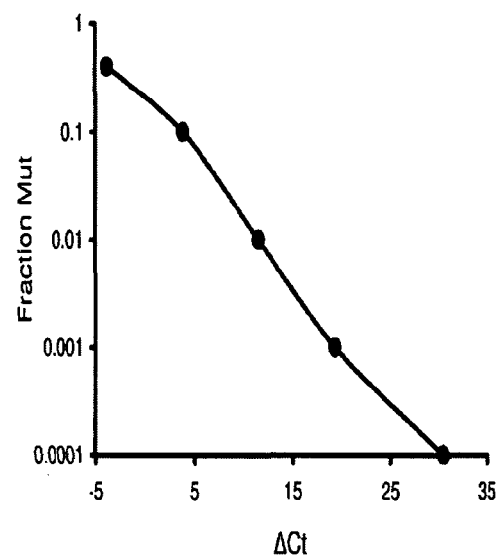
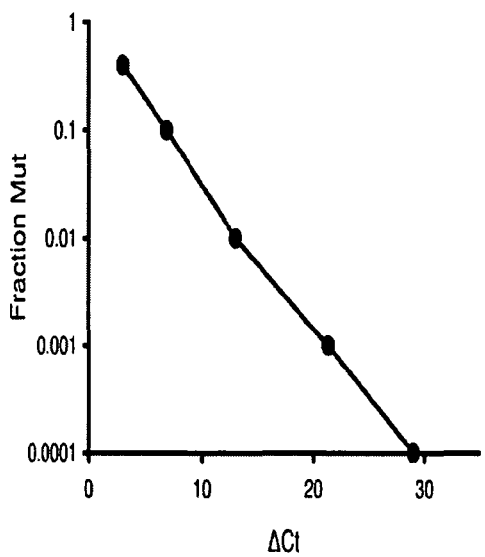
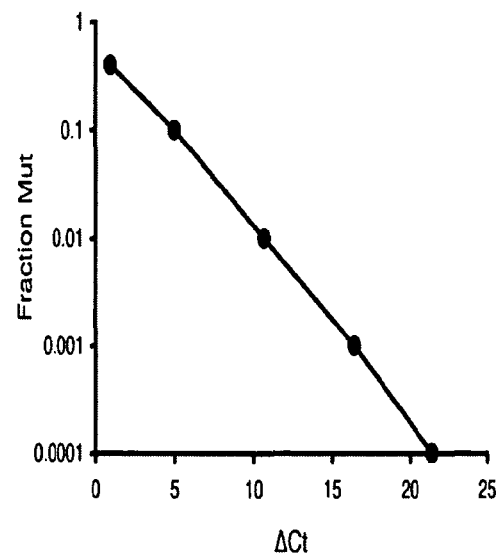

METHODS FOR DETECTION AND TYPING OF NUCLEIC ACIDS

CROSS-REFERENCE TO RELATED APPLICATIONS

This application claims the benefit under 35 U.S.C. §119 (e) to U.S. provisional application 60/688,409, filed on Jun. 7, 2005, which entire contents are incorporated herein by reference.

FIELD OF THE INVENTION

The invention relates generally to the field of detecting and typing nucleic acids. More specifically, the invention relates to detecting and typing infectious agents, such as viruses. In particular, the invention relates to the detection of HIV, and to the detection of mutations in HIV that may lead to drug resistance.

BACKGROUND

Human Immunodeficiency Virus ("HIV"), an approximately 10-kb, enveloped, single-stranded RNA retrovirus, is the causative agent of Acquired Immunodeficiency Syndrome ("AIDS"). As the HIV epidemic continues to spread world-wide, the need for effective HIV detection methods remains paramount. Early detection of HIV infection is critical for preventing the spread of the virus and concomitant disease, and for determining effective treatments and therapies. However, a key obstacle to HIV detection and treatment has been—and remains to be—the incredible variability of HIV types, and the extent and swiftness of HIV mutation (Wain-Hobson in The Evolutionary biology of Retroviruses, SSB Morse Ed. Raven Press, NY, pgs 185 209 (1994)).

Molecular characterizations have shown that the HIV virus can be categorized into two broad types. HIV-1, discovered in 1984, is the main cause of AIDS around the world, particularly in the Western Hemisphere and in Europe. HIV-2, discovered two years later in 1986, is noted mainly in western Africa. Both HIV-1 and HIV-2 are additionally categorized into sub-types. For example, HIV-2 is broken down into sub-types A-G; sub-types A and B are considered "epidemic," while C-G are considered "nonepidemic." Similarly, molecular characterization of HIV-1 strains from around the world have identified three distinct groups, M, N and O. Group M viruses represent the majority of HIV-1 and based on sequence divergence Group M has been further subdivided into nine different subtypes or clades, termed subtypes A, B, C, D, F, G, H, J, and K (Robertson, D. L. et al. In: Human Retroviruses and AIDS 1999—A Compilation and Analysis of Nucleic Acid and Amino Acid Sequences, Kuiken, C. et. al. Eds., pgs. 492-505 (1999)).

The overall distribution of HIV-1 strains varies considerably in different geographic regions and is undergoing continual change. For example, while subtype B has been predominant in North America and Western Europe (see e.g., McCutchan, F. E., AIDS 14 (suppl 3): S31-S44 (2000)), increasing numbers of non-subtype B infections are being observed in both Europe and the United States.

In addition to the great diversity of types and subtypes, drug-resistant and therapy-resistant mutants have also become prevalent. Due to the extreme mutability of the HIV virus (HIV does not employ a "proof-reading" mechanism during replication), the development of vaccines has been a major challenge, and the use of other drug therapies, such as anti-viral drugs, has been complicated by the rapid evolution of drug resistant strains.

Drug-resistance mutations have been identified in HIV-1 patients who have shown improvement under some type of drug treatment or therapy and have then experienced a "relapse" of HIV-1 viral growth and associated symptoms. Mutations associated with resistance to anti-viral drugs have been found in the gag, pol and env regions of the HIV viral genome, and have been show to affect proteins such as reverse transcriptase, protease, and the GP41 envelope protein (See e.g., Johnson, et al., 2005 Special Contribution—Drug Resistance Mutations in HIV-1, 13:3, 125-131; Gingeras et al., 1991, J. Infect. Dis. 164(6):1066-1074; Richman et al., 1991, J. Infect. Dis. 164(6):1075-1081; Schinazi et al., 1993, Antimicrob. Agents Chemother. 37(4):875-881; Najera et al., 1994, AIDS Res. Hum. Retroviruses 10(1 1):1479-1488; Eastman et al., 1995, J. AIDS Hum. Retrovirol. 9(3):264-273; Frenkel et al., 1995, J. Clin. Microbiol. 33(2):342-347; Shiras et al., 1995, Proc. Natl. Acad. Sci. USA 92(6):2398-2402; Leal et al., 1996, Eur. J. Clin. Invest. 26(6):476-480; Cleland et al., 1996, J. AIDS Hum. Retrovirol. 12(1):6-18; Schmit et al., 1996, AIDS 10(9):995-999; Vasudevechari et al., 1996, Antimicrob. Agents Chemother. 40(11):2535-2541; Winslow et al., 1996, AIDS 10(11):1205-1209; Fontenot et al., Virology 190(1):1-10; Cornelissen et al., 1997, J. Virol. 71(9): 6348-6358; Ives et al., 1997, J. Antimicrob. Chemother. 39(6):771-779).

Determining whether an HIV-1 infected patient is carrying drug-resistant viral strains may be critical for proper treatment and therapy. For example, a clinician may be able to decide whether to begin or maintain a particular antiretroviral therapy. Further, continued testing of patients for drug-resistant HIV mutants during treatment may be used to detect the emergence of a drug-resistant virus, thereby allowing the clinician to alter the therapy to something that may prove more effective. Thus, there is a need in the art for assays that provide information related to HIV drug-resistance.

SUMMARY

The methods and kits described herein relate to detecting the presence of nucleic acid in a sample. In particular, the methods and kits are useful for detecting a specific mutation in a heterogeneous population of polynucleotides. In some aspects, the methods and kits may be used to treat or diagnose viral infections in mammals. The methods and kits may relate to detecting and typing viruses that can cause Acquired Immunodeficiency Syndrome ("AIDS") or AIDS-like symptoms in mammals, such as HIV-1, using oligonucleotides having at least one non-natural nucleotide.

In some aspects, the methods and kits are used to detect a specific mutation in a heterogeneous population of polynucleotides, in which the specific mutation, if present, is located in a first region of the population. Typically, the population includes one or more additional mutations located in a second region.

The method may include amplifying the population of polynucleotides with a first set of primers to obtain an amplification product that includes the first region, in which method at least one primer of the first set of primers is capable of specifically hybridizing to the second region of the population. For example, the at least one primer of the first set of primers may be capable of specifically hybridizing to the second region of the entire population of polynucleotides as a universal primer. The method further may include amplifying the amplification product with a second set of primers to detect the mutation, in which at least one primer of the second primer set includes at least one non-natural base. In some embodiments, the primer of the second primer set may have a 3' nucleotide that is complementary to the first region if the mutation is present. Optionally, the second primer set may include a primer having a 3' nucleotide that is complementary to the first region if the mutation is absent. Typically, the at least one primer of the first primer set does not hybridize specifically to the first region of the population of polynucleotides. Typically, the at least one primer of the second primer set does hybridize specifically to the first region of the population.

In some embodiments the specific mutation includes a single base change. For example, the first region of the population of polynucleotides may consist of a single nucleotide.

In some embodiments, at least one primer of the first primer set or second primer set includes at least one non-natural base. Preferably, at least one primer of the second primer set includes at least one non-natural base. In some embodiments, the non-natural base may be selected from iC and iG. The at least one primer may include a label. For example, the label may be coupled to the non-natural base. Suitable labels include fluorophores and quenchers.

Amplification may be performed in a reaction mixture that includes at least one non-natural nucleotide having a non-natural base. The at least one non-natural nucleotide of the reaction mixture may base pair with the at least one non-natural base present in the primer of the first and/or second primer set. Optionally, the non-natural nucleotide is coupled to a label which may include fluorophores and quenchers. The quencher may quench a fluorophore present in the primer of the first and/or second primer set.

The method may be used to detect the mutation continuously during amplification or in real-time. The method may be used quantitatively.

In some embodiments, the population of polynucleotides includes a sequence of HIV-1. The mutation may be present in the HIV-1 polymerase or protease gene.

In some aspects, the methods and kits are used to detect a specific mutation in a heterogeneous population of polynucleotides, where the specific mutation, if present, is located in a first region of the population and the population includes one or more additional mutations located in a second region of the population. The method may include: (a) reacting the population and a mixture of oligonucleotides, where the mixture includes: (i) a first oligonucleotide capable of hybridizing to at least the first region of the population; and (ii) a pool of degenerate oligonucleotides capable of hybridizing to at least the second region of one or more polynucleotides of the population, where one or more oligonucleotides of the mixture include one or more non-natural bases and optionally a label; and (b) detecting the mutation. In additional aspects, the method may include: (a) reacting the population and a pool of degenerate oligonucleotides, where the oligonucleotides of the pool include one or more non-natural bases and where the pool includes: (i) at least one oligonucleotide capable of hybridizing to at least the first region of one or more polynucleotides of the population; and (ii) a plurality of oligonucleotides capable of hybridizing to at least the second region of one or more polynucleotides of the population; and (b) detecting the mutation. In some embodiments, the non-natural bases are selected from the group consisting of iso-G, iso-C and a combination thereof. The degenerate oligonucleotides may include at least one label. In some embodiments, all of the degenerate oligonucleotides include a non-natural base and a label. Suitable labels include fluorophores and quenchers.

Detecting may include amplifying one or more polynucleotides of the population. For example, detecting may include amplifying one or more polynucleotides of the population in the presence of at least one non-natural nucleotide. The non-natural nucleotide may have a non-natural base (e.g., iC and iG), which, optionally, is capable of base-pairing with the non-natural base of the mixture of oligonucleotides (e.g., a non-natural base present in the degenerate oligonucleotides). The non-natural nucleotide may be coupled to a label. Suitable labels include fluorophores and quenchers. The methods may be used to detect mutations continuously during amplification or in real-time. The heterogeneous population may include polynucleotides of HIV-1.

In some aspects, the methods and kits are used to detect the presence, and optionally the absence, of a mutation in a polynucleotide at a specific nucleotide position. The method typically includes amplifying the polynucleotide with primers to detect the presence, and optionally the absence, of the mutation. In some embodiments, the primers include: (a) a first primer having a 3' nucleotide that is complementary to the polynucleotide (at a specific nucleotide position) if the mutation is present; (b) a second primer having a 3' nucleotide that is complementary to the polynucleotide (at a specific nucleotide position) if the mutation is absent. Typically, the first primer and the second primer are not complementary to the polynucleotide at one or more positions other than the 3' nucleotide and do not include identical nucleotides at the one or more positions. For example, the first and second primer may not be complementary to each other at the one or more positions other than the 3' nucleotide. In some embodiments, at least one of the first primer and the second primer includes at least one non-natural base (e.g., iC and iG), which may be present at the one or more positions. At least one of the first primer and the second primer may include a label. Where both the first primer and second primer include a label, the label may be the same or different, preferably different. Suitable labels include fluorophores and quenchers. Optionally, the label may be coupled to the non-natural base. Amplification may be performed using a reaction mixture that includes at least one non-natural nucleotide having a non-natural base, which optionally may base-pair with the non-natural base present in the first primer, the second primer, or both primers. The non-natural nucleotide of the reaction mixture may include a label. Suitable labels may include a fluorophore and a quencher, which optionally is capable of quenching a fluorophore, if present, in at least one of the first primer and second primer, preferably both. The methods may be used to detect mutations continuously during amplification or in real-time. The mutation may include a single nucleotide polymorphism present in HIV-1 nucleic acid, e.g., in the polymerase gene or protease gene.

In some aspects, the methods and kits are used for identifying HIV-1 in a sample. The methods and kits may include (a) reacting a reaction mixture, where the reaction mixture includes: (i) the sample; (ii) at least one oligonucleotide comprising at least one non-natural base, where the oligonucleotide is capable of specifically hybridizing to HIV-1 nucleic acid; and (b) detecting HIV-1 nucleic acid if present in the sample. In some embodiments, the at least one oligonucleotide is selected from the group consisting of SEQ ID NO:2-97.

In some aspects, the methods and kits relate to detecting specific mutations in heterogeneous, (e.g., polymorphic) populations of polynucleotides. By way of example, but not by way of limitation, the methods may be used to detect a specific mutation, such as a drug resistance mutation, in a heterogeneous population of HIV polynucleotides, such as HIV-1 polynucleotides. In some methods, the specific mutation may be a single base change, such as a transition or transversion. In other methods the specific mutation may be an insertion, a deletion or a rearrangement. Thus, the mutation if present, may be located in a first region of the population and the population may include one or more additional mutations located in a second region. In some methods, the "first region" may be only a single nucleotide.

To detect a mutation in such a polymorphic or heterogeneous population, the methods may include the steps of (a) amplifying the population with a first set of primers to obtain an amplification product, where at least one primer of the first set of primers may be capable of specifically hybridizing to the second region of the population; and (b) amplifying the product with a second set of primers to detect the mutation, where at least one primer of the second primer set may include at least one non-natural nucleotide.

In some embodiments, the at least one primer of the first primer set may not hybridize specifically to the first region of the population. In other methods, at least one primer of the first set of primers may include at least one non-natural nucleotide.

In other embodiments, the at least one primer of the second primer set may specifically hybridize to the first region of the population. In still other embodiments, the at least one primer of the second primer set, which may include at least one non-natural nucleotide, may also include a label. In further embodiments, the label may be a fluorophore. In some embodiments, amplifying the product with the second set of primers may include amplifying in the presence of at least one quencher coupled to a non-natural nucleotide. The methods of detecting a specific mutation may also include reverse transcription, amplification, and real-time detection. Some methods may include amplification in the presence of a quencher coupled to a non-natural nucleotide.

In some aspects, the methods and kits also relate to detecting a specific mutation in a heterogeneous population of polynucleotides using degenerate oligonucleotides. Such methods may include the steps of (a) reacting the population of heterogeneous polynucleotides, such as, for example HIV-1 polynucleotides, and a pool of degenerate oligonucleotides to detect the mutation. In some embodiments, the oligonucleotides of the pool may include one or more non-natural nucleotides, for example, iso-GTP ("iGTP"), iso-CTP ("iCTP") and combinations thereof. The degenerate oligonucleotides may further include at least one label, such as, for example, a fluorophore. The pool of degenerate oligonucleotides may include (i) at least one oligonucleotide capable of hybridizing to the first region of one or more polynucleotides of the population; and (ii) a plurality of oligonucleotides capable of hybridizing to the second region of one or more polynucleotides of the population.

In some embodiments, detecting the specific mutation may include reverse transcription, amplification and/or real time detection of one or more polynucleotides of the population. Amplification may be performed in the presence of one or more non-natural nucleotides and/or in the presence of at least one quencher coupled to a non-natural nucleotide. In some embodiments, the non-natural nucleotide coupled to the at least one quencher may be iCTP or iGTP.

The methods and kits also relate to detecting the presence or absence of a mutation, at a specific nucleotide, in a polynucleotide. By way of example, but not by way of limitation, the methods may include detecting the presence or absence of a mutation, such as a drug resistance mutation, in an HIV polynucleotide such as HIV-1.

Such methods of detecting the presence or absence of a mutation may include amplifying the polynucleotide with primers. In these methods, the primers may include (a) a first primer having a 3' nucleotide that is complementary to the specific nucleotide where the mutation is present and capable of amplifying the polynucleotide; and (b) a second primer having a 3' nucleotide that is complementary to the specific nucleotide where the mutation is absent and capable of amplifying the polynucleotide. In some embodiments, the first primer and the second primer may include nucleotides that are non-complementary to the polynucleotide at one or more positions other than the 3' nucleotide. In other embodiments, the first and the second primers may include non-complementary nucleotides at different positions. In still other embodiments, the first and the second primers may include different non-complementary nucleotides at the same position. For example, in some embodiments, the first primer and the second primer are not complementary to the polynucleotide at a single position other than the 3' nucleotide and also do not include identical nucleotides at that single position.

In some embodiments, at least one of the first primer and the second primer may include at least one non-natural nucleotide. For example, the at least one non-natural nucleotide may be at the one or more non-complementary positions. Any non-natural nucleotide may be used; however, in some embodiments, iso-G, iso-C and combinations thereof may be preferred. In still other embodiments one or more of the primers may include a label; in some embodiments, the labels on each primer may be different. In some embodiments, at least one label may be a fluorophore. In some methods, detection may include reverse transcription, amplification and/or real time detection. In some embodiments, amplification may be performed in the presence of a quencher coupled to a non-natural base or non-natural base triphosphate.

Some methods may include an oligonucleotide that functions as an internal control nucleic acid. In other methods, the reaction mixture may include at least two oligonucleotides capable of hybridizing to an internal control nucleic acid and that may function as primers to amplify the internal control nucleic acid. In some methods, at least one of the two oligonucleotides used as a primer for the internal control may include at least one base or nucleotide other than A, C, G, T and U. For example, the nucleotide may include iso-cytosine and/or iso-guanine ("iC" and/or "iG," respectively). In some methods, at least one of the oligonucleotides used as a primer for the internal control may includes a second label. Suitable labels may include fluorophores and quenchers. In other methods, the reaction mixture may include a nucleotide covalently linked to a second quencher, which may be the same or different as the first quencher. For example, the reaction mixture may include a non-natural nucleotide (e.g., a nucleotide having iC or iG as a base) covalently linked to a quencher.

In some methods, the first and second labels may be different. In some methods the first and second quencher may be different and may be capable of quenching two different fluorophores. In other methods, the first and second quenchers may be the same and may be capable of quenching two different fluorophores.

The methods and kits described herein also relate to detecting the presence or absence of one or more mutations in a nucleic acid sample, such as HIV. Some of these mutations may confer drug-resistance in HIV-infected mammals. By way of example, but not by way of limitation, drug resistance may include resistance to one or more of the following: azidothymidine ("AZT"), didanosine ("DDI"), tenofovir ("TDF"), amdoxovir ("DAPD"), lamivudine ("3TC"), emtricitabine ("FTC"), zalcitabine ("DOC"), saquinavir, nelfinavir, aprenavir, non-nucleoside reverse transcriptase inhibitors, multi-drug resistance, and a combination thereof. The methods and kits may include multiplex assays that are capable of detecting wild-type HIV nucleic acid and HIV nucleic acid having one or more mutations (e.g., mutations in HIV reverse transcriptase nucleic acid and/or mutations in HIV protease nucleic which, in some embodiments, may correspond with drug resistance).

In some aspects, the methods and kits may be used to detect HIV nucleic acid. One method for detecting HIV nucleic acid and for detecting the presence or absence of one or more mutations in HIV nucleic acid may include reacting a mixture which includes: 1) HIV nucleic acid isolated from a sample, and 2) at least one oligonucleotide that is capable of specifically hybridizing to the viral nucleic acid, where the oligonucleotide includes at least one non-natural base. In some methods, the at least one oligonucleotide may specifically hybridize to HIV wild-type or HIV mutant nucleic acid sequence.

Other methods for detecting HIV may include reacting a mixture including HIV nucleic acid isolated from a sample, a control nucleic acid, and at least two pairs of oligonucleotides. In some methods, the first pair of oligonucleotides may be capable of hybridizing to the viral nucleic acid, and the second pair of oligonucleotides may be capable of hybridizing to the control nucleic acid, and at least one oligonucleotide of each pair of oligonucleotides may include a label that is different from the label of the other oligonucleotide pairs, and at least one oligonucleotide of each pair of oligonucleotides may include at least one non-natural nucleotide. In another method, the viral nucleic acid and the control nucleic acid may be amplified and detected. In still another method, kits may be provided for the detection of HIV infection in a mammal.

The methods may be used to detect a viral agents such as HIV or a virus that is capable of causing AIDS or AIDS-like symptoms. For example, the viral agent may include HIV having the genomic sequence provided as GenBank Accession No. M19921, or natural or artificial variants thereof. For example, a natural or artificial variant may include a virus having at least about 95% genomic sequence identity to the genomic sequence, or regions of the genomic sequence (e.g., the pol region, the reverse transcriptase sequence or the protease sequence) deposited as GenBank Accession No. M19921. A natural or artificial variant may include a virus whose genome, or regions of the genome (e.g., the pol region, the reverse transcriptase sequence or the protease sequence) hybridizes to the genomic sequence deposited as GenBank Accession No. M19921 under stringent conditions.

For example, some embodiments of the methods may utilize at least one oligonucleotide including at least one non-natural nucleotide that is capable of hybridizing to the genomic sequence of HIV (e.g., under stringent conditions). The oligonucleotide may be capable of specifically hybridizing to sequences in the HIV pol region, for example, the oligonucleotide may hybridize to the HIV reverse transcriptase sequence, or the HIV protease sequence. In some methods, the oligonucleotides of the present methods may be capable of hybridizing to a HIV nucleotide sequence that encodes the sequences represented by SEQ ID NO. 1. In other methods, the oligonucleotide may be capable of specifically hybridizing to a natural or artificial variant of the nucleotide sequence that encodes SEQ ID NO 1.

In some embodiments, the at least one oligonucleotide including at least one non-natural nucleotide may be capable of specifically hybridizing to mutant genomic sequences of HIV (e.g., under stringent conditions). In some embodiments, the one or more mutations may be in the pol region of the HIV genome. For example, the one or more mutants may be in the reverse transcriptase gene, the protease gene or both. In other methods, the one or more mutations may include M41L, T215Y, T215F, K65R, L74V, T69D, E44K, V118I, M184V, M184I, L100I, K103N, Y181C, Y181I, Y188L, M46I, L90M, G48V, D30N, and 150V. In some methods, at least one of the oligonucleotides may be SEQ ID NO: 4, 7, 10, 13, 16, 19, 22, 25, 28, 31, 34, 37, 40, 43, 46, 49, 52, 55, 58, 61, 64, 67, 70, 73 and 74. In some embodiments, the presence or absence of one or more mutations is determined relative to the HIV-1 encoded by Genbank Accession No. M19921.

Some methods for determining the presence or absence of one or more mutations in HIV may include reacting a reaction mixture which includes HIV nucleic acid isolated from a sample and a first oligonucleotide containing at least one non-natural nucleotide which may be capable of detecting a wild-type HIV sequence at a first location, and a second oligonucleotide containing at least one non-natural nucleotide which may be capable of detecting a mutant HIV sequence at the first location. In some methods, the oligonucleotide pairs may include SEQ ID NO: 3, 4; 6, 7; 9, 10; 12, 13; 15, 16; 18, 19; 21, 22; 24, 25; 27, 28; 30, 31; 33, 34; 36, 37; 39, 40; 42, 43; 45, 46; 48, 49; 51, 52; 54, 55; 57, 58; 60, 61; 63, 64; 66, 67; 69, 70; 72, 73; and degenerate oligonucleotide pairs, for example, oligonucleotides modeled from oligonucleotide SEQ ID NO: 74. In some methods, each oligonucleotide of the oligonucleotide pair may include at least one label. In some methods, the labels may be different.

In some methods, the reaction mixture may include at least two oligonucleotides that are capable of hybridizing to the HIV nucleic acid and that may function as primers for the amplification of HIV nucleic acid. In some methods, at least one of the two oligonucleotides is used as a primer and includes at least one base or nucleotide other than A, C, G, T and U; the base or nucleotide may include iC or iG (e.g., diCTP or diGTP). In some methods, at least one of the oligonucleotides used as a primer may include a first label. Suitable labels may include fluorophores and quenchers. In some methods, the reaction mixture may include a nucleotide (e.g. a non-natural nucleotide) covalently linked to a first quencher. The non-natural nucleotide may include a non-natural base such as iC or iG.

In some embodiments, the methods may include performing reverse transcription of target RNA, for example, HIV RNA. In other embodiments, the methods may include performing an amplification (e.g., PCR which may include RT-PCR). The methods may include hybridizing a probe to an amplified nucleic acid to detect an amplified target. For example, the methods may include performing RT-PCR followed by performing probe hybridization.

The methods described herein may include determining a melting temperature for an amplicon (e.g., amplified nucleic acid of at least one of amplified nucleic acid of HIV and amplified control nucleic acid). The methods may include determining a melting temperature for a nucleic acid complex that includes a labeled probe hybridized to a target nucleic acid (which may include amplified target nucleic acid). The melting temperature may be determined by exposing the amplicon or nucleic acid complex to a gradient of temperatures and observing a signal from a label. Optionally, the melting temperature may be determined by (a) reacting an amplicon with an intercalating agent at a gradient of temperatures and (b) observing a detectable signal from the intercalating agent. The melting temperature of a nucleic acid complex may be determined by (1) hybridizing a probe to a target nucleic acid to form a nucleic acid complex, where at least one of the probe and the target nucleic acid includes a label; (2) exposing the nucleic acid complex to a gradient of temperatures; and (3) observing a signal from the label.

The methods may be performed in any suitable reaction chamber under any suitable conditions. For example, the methods may be performed in a reaction chamber without opening the reaction chamber. The reaction chamber may be part of an array of reaction chambers. In some embodiments, the steps of the methods may be performed separately in different reaction chambers.

In some aspect, the methods may utilize and/or the kits may include a first pair of oligonucleotides capable of hybridizing to a HIV nucleic acid. In some embodiments, at least one oligonucleotide of the first pair may include at least one non-natural nucleotide; in other embodiments, the oligonucleotide may also include at least one label. In further embodiments, a kit may also include control nucleic acid and a second pair of oligonucleotides capable of hybridizing to the control nucleic acid. In some embodiments, at least one oligonucleotide of the second pair may include at least one non-natural nucleotide and a second label. In some embodiments, the first and second label may be different.

In some embodiments, the methods may be capable of detecting no more than about 100 copies of the target nucleic acid in a sample (e.g., in a sample having a volume of about 25 microliters). In other embodiments, the methods may be capable of detecting no more than about 500 copies, 1000 copies, 5000 copies, or 10,000 copies in a sample (e.g., in a sample having a volume of about 25 microliters).

In other embodiments, the methods may be capable of detecting no more than about 100 copies of target nucleic acid in a sample (e.g., in a sample having a volume of about 25 microliters) using real-time detection in no more than about 150 cycles of the PCR, no more than about 100 cycles, no more than about 90 cycles, no more than about 80 cycles, no more than about 70 cycles, no more than about 60 cycles, no more than about 50 cycles, no more than about 40 cycles, or no more than about 30 cycles of the PCR.

Typically, the methods may be capable of detecting a nucleic acid target such as a DNA or an RNA target in a sample, when the target represents about 1%-10% of the total molecules present in the sample. In some embodiments, the methods may be capable of detecting a nucleic acid target such as a DNA or an RNA target in a sample, when the target represents about 0.5%-5% of the total molecules present in the sample (or about 0.1% to about 1%).

In some embodiments, the methods and kits related to detecting a target that includes a mutation. Detected mutations may include a single-base change, a deletion, insertion and/or rearrangement.

BRIEF DESCRIPTION OF THE DRAWINGS

FIG. 1 is an exemplary amino acid sequence of an HIV-1 pol polyprotein, Genbank Accession No. M19921, (SEQ ID NO:1).

FIGS. 3A and 3B show $\Delta C_t$ vs. fraction mutant plots for real-time PCR runs with 4 different cycling conditions and 2 different instruments.

In FIG. 5, the black bars represent samples tested with 100% wild-type target (M184M); the dark grey bars represents samples tested with 50% wild-type and 50% mutant target; the light gray bars represent samples tested with 100% mutant target (M184V). In FIG. 6, the number of iso-Gs in the wild-type primer ("wt") is on the top row of the X axis, the number of iso-Gs in the mutant primer ("mt") is on the bottom row of the Y axis. In FIG. 6, the black bars represent samples tested with 100% wild-type target (M184M); the dark grey bars indicate samples tested with 10% mutant target (M184V); and the light grey bars indicate samples tested with 100% mutant target (M184V).

DETAILED DESCRIPTION

Figure 2:
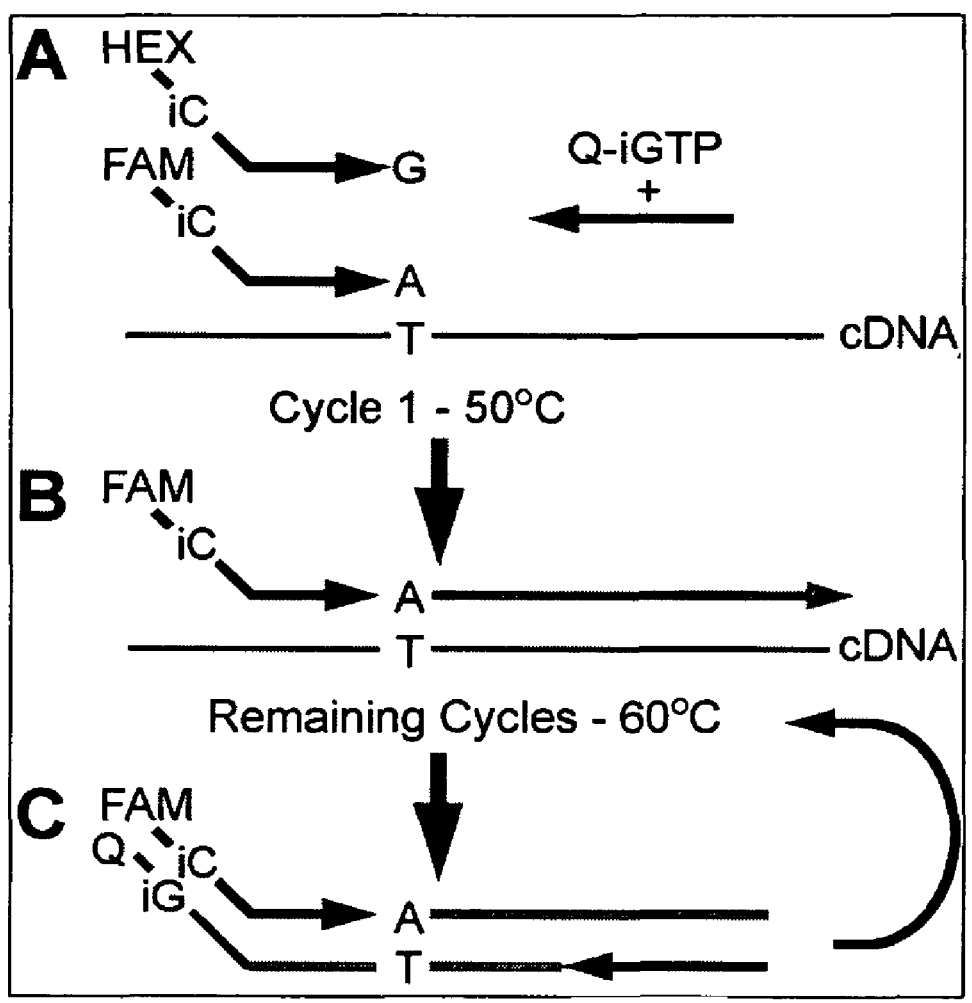
FIG. 2 is a schematic representation of an exemplary HIV detection method ("MultiCode-RTx" genotyping and detection schematic) employing at least one oligonucleotide with at least one non-natural base. A. In this example, cDNA targets are amplified in the presence of iGTP-dabcyl (Q-iGTP), one standard reverse and two RTx forward primers. The two forward primers are bipartite. In this example, the 5'-parts contain single iCs, separable fluorescent reporters and target independent sequence tails that add 10° C. to the annealing temperature of each primer. The 3'-parts are target-specific, contain a 3' mutation-specific base (A or G) and have an annealing temperature of 50° C. to the cDNA targets. B. A single round of competitive priming at 50° C. results in specific extension (gray arrow) creating the A:T target. C. Remaining cycles at 60° C. inhibit annealing of the G-primer and place quenchers in close proximity to the reporter.

Disclosed are methods and kits for detecting nucleic acids in a sample. Typically, the methods include detecting signals such as a signal emitted from a fluorophore. Also disclosed are oligonucleotides, especially primers and probes, which may be used for the detection of viruses capable of causing AIDS or AIDS-like symptoms. The methods, kits, and oligonucleotides disclosed herein may be used to detect HIV, which has been shown to be the causative agent of AIDS in humans. Additionally, some methods may be based on assay methods described in published international application WO 01/90417, U.S. published application 2002/0150900, and Moser et al., *Antimicrobial Agents and Chemotherapy*, 2005, 49(8):3334-35, herein incorporated by reference in their entireties.

As used herein, unless otherwise stated, the singular forms "a," "an," and "the" includes plural reference. Thus, for example, a reference to "an oligonucleotide" includes a plurality of oligonucleotide molecules, and a reference to "a nucleic acid" is a reference to one or more nucleic acids.

As used herein, the term "sample" is used in its broadest sense. A sample may include a bodily tissue or a bodily fluid including but not limited to blood (or a fraction of blood such as plasma or serum), lymph, mucus, tears, urine, and saliva. A sample may include an extract from a cell, a chromosome, organelle, or a virus. A sample may comprise DNA (e.g., genomic DNA), RNA (e.g., mRNA), and cDNA, any of which may be amplified to provide amplified nucleic acid. A sample may include nucleic acid in solution or bound to a substrate (e.g., as part of a microarray). A sample may comprise material obtained from an environmental locus (e.g., a body of water, soil, and the like) or material obtained from a fomite (i.e., an inanimate object that serves to transfer pathogens from one host to another).

The term "source of nucleic acid" refers to any sample which contains nucleic acids (RNA or DNA). Particularly preferred sources of target nucleic acids are biological samples including, but not limited to blood, plasma, serum, saliva, cerebral spinal fluid, pleural fluid, milk, lymph, sputum and semen.

As used herein, the term "limit of detection" refers to the lowest level or amount of an analyte, such as a nucleic acid, that can be detected and quantified. Limits of detection can be represented as molar values (e.g., 2.0 nM limit of detection), as gram measured values (e.g., 2.0 microgram limit of detection under, for example, specified reaction conditions), copy number (e.g., $1 \times 10^5$ copy number limit of detection), or other representations known in the art.

As used herein, "HIV" is meant to include any retrovirus that is capable of infecting a mammal and that has been shown to be the causative agent of Acquired Immunodeficiency Syndrome ("AIDS") or AIDS-like symptoms. The terms "HIV-1" or "HIV-2" are meant to include all types and sub-types of HIV-1 and HIV-2. That is, if the term HIV-1 is used, it is meant to encompass all types (e.g., M, N and O) and sub-types (e.g., A-K), and natural and artificial variants of these type and subtypes. By way of example, but not by way of limitation, an exemplary HIV sequence is provided by Genbank Accession No. M19921. Natural and artificial variants of this sequence are contemplated in the methods and kits, and may include, for example, silent mutations and mutations that confer drug resistance.

As used herein, the term "pol region" or "pol gene" means that region of the HIV genome which includes the coding sequence for at least a reverse transcriptase and a protease. By way of example, but not by way of limitation, an exemplary pol region polyprotein amino acid sequence is shown in FIG. 1, SEQ ID NO: 1. In some embodiments, the sequence of the detected HIV may have about 95% sequence identity to SEQ ID NO 1. In other embodiments, the sequence of the detected HIV may have about 90% sequence identity to SEQ ID NO: 1. In still other embodiments, the sequence of the detected HIV may have about 80% sequence identity to SEQ ID NO: 1.

As used herein the term "isolated" in reference to a nucleic acid molecule refers to a nucleic acid molecule which is separated from the organisms and biological materials (e.g., blood, cells, serum, plasma, saliva, urine, stool, sputum, nasopharyngeal aspirates and so forth), which are present in the natural source of the nucleic acid molecule. An isolated nucleic acid molecule, such as a cDNA molecule, can be substantially free of other cellular material, or culture medium when produced by recombinant techniques, or substantially free of chemical precursors or other chemicals when chemically synthesized. In some embodiments, nucleic acid molecules encoding polypeptides/proteins may also be isolated or purified. Methods of nucleic acid isolation are well known in the art and may include total nucleic acid isolation/purification methods, RNA-specific isolation/purification methods or DNA-specific isolation/purification methods.

As used herein, the term "isolated virus" refers to a virus which is separated from other organisms and biological materials which are present in the natural source of the virus, e.g., biological material such as cells, blood, serum, plasma, saliva, urine, stool, sputum, nasopharyngeal aspirates, and so forth. The isolated virus can be used to infect a subject.

As used herein, the term "subject" is refers to an animal, preferably a mammal, more preferably a human. The term "subject" and "patient" may be used interchangeably.

A "mutation" is meant to encompass at least a single nucleotide variation in a nucleic acid sequence relative to the normal sequence or wild-type sequence. A mutation may include a substitution, a deletion, an inversion or an insertion. With respect to an encoded polypeptide, a mutation may be "silent" and result in no change in the encoded polypeptide sequence or a mutation may result in a change in the encoded polypeptide sequence. For example, a mutation may result in a substitution in the encoded polypeptide sequence. A mutation may result in a frameshift with respect to the encoded polypeptide sequence. For example, the HIV virus of the present methods may be mutants as compared to the HIV virus nucleic acid of Genbank Accession No. M19921 or other known HIV virus strains.

Some mutations may confer drug resistance in HIV infected mammals, subjects or patients. As used herein the term "drug resistant" means the ability of an infectious agent to withstand a drug to which it was once sensitive and was either slowed in growth and proliferation or killed outright. By way of example, but not by way of limitation, drug resistance with respect to HIV infection may include resistance to one or more of the following: azidothymidine, didanosine, tenofovir, amdoxovir, lamivudine, emtricitabine, zalcitabine, saquinavir, nelfinavir, aprenavir, non-nucleoside reverse transcriptase inhibitors, multi-drug resistance, and a combination thereof.

Mutations, and drug resistance mutations, may be in any region of the HIV genome. For example, mutations may be in the pol region, and may include mutations in the reverse transcriptase gene and/or the protease gene. By way of example, but not by way of limitation, some exemplary mutations may include M41L, T215Y, T215F, K65R, L74V, T69D, E44K, V118I, M184V, M184I, L100I, K103N, Y181C, Y181I, Y188L, M46I, L90M, G48V, D30N, and I50V.

As used herein, the term "microarray" refers to an arrangement of a plurality of polynucleotides, polypeptides, or other chemical compounds on a substrate. The terms "element" and "array element" refer to a polynucleotide, polypeptide, or other chemical compound having a unique and defined position on a microarray.

As used herein, an oligonucleotide is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, made up of "dNTPs," which do not have a hydroxyl group at the 2' position, and oligoribonucleotides, made up of "NTPs," which have a hydroxyl group in this position. Oligonucleotides also may include derivatives, in which the hydrogen of the hydroxyl group is replaced with organic groups, e.g., an allyl group.

In some embodiments, oligonucleotides as described herein may include a peptide backbone. For example, the oligonucleotides may include peptide nucleic acids or "PNA." Peptide nucleic acids are described in WO 92/20702, which is incorporated herein by reference.

An oligonucleotide is a nucleic acid that includes at least two nucleotides. Oligonucleotides used in the methods disclosed herein typically include at least about ten (10) nucleotides and more typically at least about fifteen (15) nucleotides. Preferred oligonucleotides for the methods disclosed herein include about 10-25 nucleotides. An oligonucleotide may be designed to function as a "primer." A "primer" is a short nucleic acid, usually a ssDNA oligonucleotide, which may be annealed to a target polynucleotide by complementary base-pairing. The primer may then be extended along the target DNA or RNA strand by a polymerase enzyme, such as a DNA polymerase enzyme. Primer pairs can be used for amplification (and identification) of a nucleic acid sequence (e.g., by the polymerase chain reaction (PCR)). An oligonucleotide may be designed to function as a "probe." A "probe" refers to an oligonucleotide, its complements, or fragments thereof, which is used to detect identical, allelic or related nucleic acid sequences. Probes may include oligonucleotides which have been attached to a detectable label or reporter molecule. Typical labels include fluorescent dyes, quenchers, radioactive isotopes, ligands, scintillation agents, chemiluminescent agents, and enzymes.

An oligonucleotide may be designed to be specific for a target nucleic acid sequence in a sample. For example, an oligonucleotide may be designed to include "antisense" nucleic acid sequence of the target nucleic acid. As used herein, the term "antisense" refers to any composition capable of base-pairing with the "sense" (coding) strand of a specific target nucleic acid sequence. An antisense nucleic acid sequence may be "complementary" to a target nucleic acid sequence. As used herein, "complementarity" describes the relationship between two single-stranded nucleic acid sequences that anneal by base-pairing. For example, 5'-AGT-3' pairs with its complement, 3'-TCA-5'. In some embodiments, primers or probes may be designed to include mismatches at various positions. As used herein, a "mismatch" means a nucleotide pair that does not include the standard Watson-Crick base pairs, or nucleotide pairs that do not preferentially form hydrogen bonds. The mismatch may include a natural nucleotide or a non-natural nucleotide substituted across from a particular base or bases in a target. For example, the probe or primer sequence 5'-AGT-3' has a single mismatch with the target sequence 3'-ACA-5'. The 5' "A" of the probe or primer is mismatched with the 3' "A" of the target. Similarly, the target sequence 5'-AGT-3' has a single mismatch with the probe or primer sequence 3'-(iC)CT-5'. Here an iso-C is substituted in place of the natural "T." However, the sequence 3'-(iC)CT-5' is not mismatched with the sequence 5'-(iG)GA-3'.

Oligonucleotides may also be designed as degenerate oligonucleotides. As used herein "degenerate oligonucleotide" is meant to include a population, pool, or plurality of oligonucleotides comprising a mixture of different sequences where the sequence differences occur at a specified position in each oligonucleotide of the population. For example degenerate oligonucleotides may be represented as GAC-ATRGTYATCTATCARTAYR (SEQ ID NO: 74), where, for example R=A or G, Y=C or T. Accordingly, the sequence of the population of oligonucleotides would be identical except for difference introduced at positions represented by "R" and "Y." The various substitutions may include any natural or non-natural nucleotide, and may include any number of different possible nucleotides at any given position. For example the above degenerate oligonucleotide may instead include R=iC or iG, or R=A or G or T or C or iC or iG.

Oligonucleotides as described herein typically are capable of forming hydrogen bonds with oligonucleotides having a complementary base sequence. These bases may include the natural bases such as A, G, C, T and U, as well as artificial, non-standard or non-natural bases such as iso-cytosine and iso-guanine. As described herein, a first sequence of an oligonucleotide is described as being 100% complementary with a second sequence of an oligonucleotide when the consecutive bases of the first sequence (read 5'→3') follow the Watson-Crick rule of base pairing as compared to the consecutive bases of the second sequence (read 3'→5'). An oligonucleotide may include nucleotide substitutions. For example, an artificial base may be used in place of a natural base such that the artificial base exhibits a specific interaction that is similar to the natural base.

An oligonucleotide that is specific for a target nucleic acid also may be specific for a nucleic acid sequence that has "homology" to the target nucleic acid sequence. As used herein, "homology" refers to sequence similarity or, interchangeably, sequence identity, between two or more polynucleotide sequences or two or more polypeptide sequences. The terms "percent identity" and "% identity" as applied to polynucleotide sequences, refer to the percentage of residue matches between at least two polynucleotide sequences aligned using a standardized algorithm (e.g., BLAST).

An oligonucleotide that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Equations for calculating Tm, for example nearest-neighbor parameters, and conditions for nucleic acid hybridization are known in the art.

As used herein "target" or "target nucleic acid" refers to a nucleic acid molecule containing a sequence that has at least partial complementarity with an oligonucleotide, for example a probe or a primer. A "target" sequence may include a part of a gene or genome.

As used herein, "nucleic acid," "nucleotide sequence," or "nucleic acid sequence" refer to a nucleotide, oligonucleotide, polynucleotide, or any fragment thereof and to naturally occurring or synthetic molecules. These terms also refer to DNA or RNA of genomic or synthetic origin which may be single-stranded or double-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. RNA may be used in the methods described herein and/or may be converted to cDNA by reverse-transcription for use in the methods described herein.

As used herein, "amplification" or "amplifying" refers to the production of additional copies of a nucleic acid sequence. Amplification is generally carried out using polymerase chain reaction (PCR) technologies known in the art. The term "amplification reaction system" refers to any in vitro means for multiplying the copies of a target sequence of nucleic acid. The term "amplification reaction mixture" refers to an aqueous solution comprising the various reagents used to amplify a target nucleic acid. These may include enzymes (e.g., a thermostable polymerase), aqueous buffers, salts, amplification primers, target nucleic acid, and nucleoside triphosphates, and optionally at least one labeled probe and/or optionally at least one agent for determining the melting temperature of an amplified target nucleic acid (e.g., a fluorescent intercalating agent that exhibits a change in fluorescence in the presence of double-stranded nucleic acid).

The amplification methods described herein my include "real-time monitoring" or "continuous monitoring." These terms refer to monitoring multiple times during a cycle of PCR, preferably during temperature transitions, and more preferably obtaining at least one data point in each temperature transition. The term "homogeneous detection assay" is used to describe an assay that includes coupled amplification and detection, which may include "real-time monitoring" or "continuous monitoring."

Amplification of nucleic acids may include amplification of nucleic acids or subregions of these nucleic acids. For example, amplification may include amplifying portions of nucleic acids between 30 and 50, between 50 and 100, between 100 and 300 bases long by selecting the proper primer sequences and using the PCR.

The disclosed methods may include amplifying at least one or more nucleic acids in the sample. In the disclosed methods, amplification may be monitored using real-time methods.

Amplification mixtures may include natural nucleotides (including A, C, G, T, and U) and non-natural nucleotides (e.g., including iC and iG). DNA and RNA are oligonucleotides that include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytosine (C), and uridine (U). These five bases are "natural bases." According to the rules of base pairing elaborated by Watson and Crick, the natural bases can hybridize to form purine-pyrimidine base pairs, where G pairs with C and A pairs with T or U. These pairing rules facilitate specific hybridization of an oligonucleotide with a complementary oligonucleotide.

The formation of these base pairs by the natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural or non-natural bases used herein can be derivatized by substitution at non-hydrogen bonding sites to form modified natural or non-natural bases. For example, a natural base can be derivatized for attachment to a support by coupling a reactive functional group (for example, thiol, hydrazine, alcohol, amine, and the like) to a non-hydrogen bonding atom of the base. Other possible substituents include, for example, biotin, digoxigenin, fluorescent groups, alkyl groups (e.g., methyl or ethyl), and the like.

Non-natural bases, which form hydrogen-bonding base pairs, can also be constructed as described, for example, in U.S. Pat. Nos. 5,432,272; 5,965,364; 6,001,983; 6,037,120; U.S. published Application No. 2002/0150900; and U.S. Pat. No. 6,140,496, all of which are incorporated herein by reference. Suitable bases and their corresponding base pairs may include the following bases in base pair combinations (iso C/iso G, K/X, H/J, and M/N):

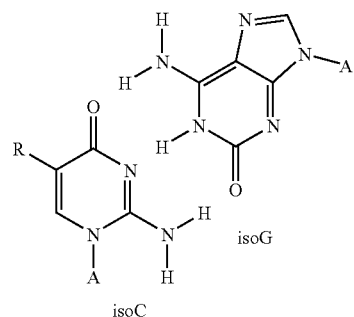

isoC   isoG

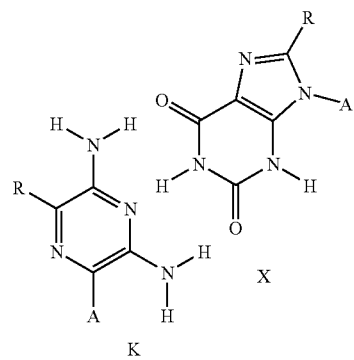

K   X

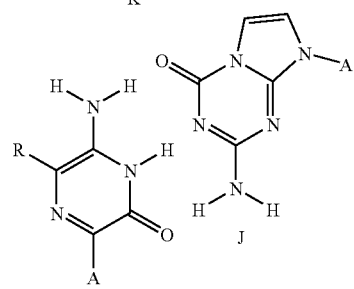

H   J

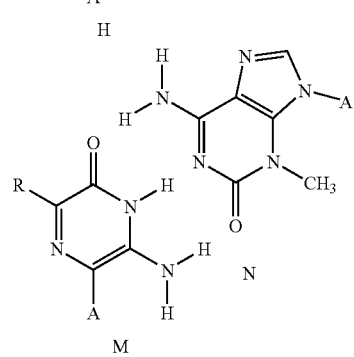

M   N

Where A is the point of attachment to the sugar or other portion of the polymeric backbone and R is H or a substituted or unsubstituted alkyl group. It will be recognized that other non-natural bases utilizing hydrogen bonding can be prepared, as well as modifications of the above-identified non-natural bases by incorporation of functional groups at the non-hydrogen bonding atoms of the bases.

The hydrogen bonding of these non-natural base pairs is similar to those of the natural bases where two or three hydrogen bonds are formed between hydrogen bond acceptors and hydrogen bond donors of the pairing non-natural bases. One of the differences between the natural bases and these non-natural bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-natural bases for use in oligonucleotides include, for example, naphthalene, phenanthrene, and pyrene derivatives as discussed, for example, in Ren, et al., *J. Am. Chem. Soc.* 1996, 118:1671 and McMinn et al., *J. Am. Chem. Soc.* 1999, 121:11585, both of which are incorporated herein by reference. These bases do not utilize hydrogen bonding for stabilization, but instead rely on hydrophobic or van der Waals interactions to form base pairs.

The use of non-natural bases according to the methods disclosed herein is extendable beyond the detection and quantification of nucleic acid sequences present in a sample. For example, non-natural bases can be recognized by many enzymes that catalyze reactions associated with nucleic acids. While a polymerase requires a complementary nucleotide to continue polymerizing an extending oligonucleotide chain, other enzymes do not require a complementary nucleotide. If a non-natural base is present in the template and its complementary non-natural base is not present in the reaction mix, a polymerase will typically stall (or, in some instances, misincorporate a base when given a sufficient amount of time) when attempting to extend an elongating primer past the non-natural base. However, other enzymes that catalyze reactions associated with nucleic acids, such as ligases, kinases, nucleases, polymerases, topoisomerases, helicases, and the like can catalyze reactions involving non-natural bases. Such features of non-natural bases can be taken advantage of, and are within the scope of the presently disclosed methods and kits.

For example, non-natural bases can be used to generate duplexed nucleic acid sequences having a single strand overhang. This can be accomplished by performing a PCR reaction to detect a target nucleic acid in a sample, the target nucleic acid having a first portion and a second portion, where the reaction system includes all four naturally occurring dNTP's, a first primer that is complementary to the first portion of the target nucleic acid, a second primer having a first region and a second region, the first region being complementary to the first portion of the target nucleic acid, and the second region being noncomplementary to the target nucleic acid. The second region of the second primer comprises a non-natural base. The first primer and the first region of the second primer hybridize to the target nucleic acid, if present. Several rounds of PCR will produce an amplification product containing (i) a double-stranded region and (ii) a single-stranded region. The double-stranded region is formed through extension of the first and second primers during PCR. The single-stranded region includes the one or more non-natural bases. The single-stranded region of the amplification product results because the polymerase is not able to form an extension product by polymerization beyond the non-natural base in the absence of the nucleotide triphosphate of the complementary non-natural base. In this way, the non-natural base functions to maintain a single-stranded region of the amplification product.

A polymerase can, in some instances, misincorporate a base opposite a non-natural base. In some embodiments, the misincorporation takes place because the reaction mix does not include a complementary non-natural base. Therefore, if given sufficient amount of time, the polymerase can, in some cases, misincorporate a base that is present in the reaction mixture opposite the non-natural base.

The nucleotides disclosed herein, which may include non-natural nucleotides, may be coupled to a label (e.g., a quencher or a fluorophore). Coupling may be performed using methods known in the art.

The oligonucleotides of the present methods may function as primers. In some embodiments, the oligonucleotides are labeled. For example, the oligonucleotides may be labeled with a reporter that emits a detectable signal (e.g., a fluorophore). The oligonucleotides may include at least one non-natural nucleotide. For example, the oligonucleotides may include at least one nucleotide having a base that is not A, C, G, T, or U (e.g., iC or iG). Where the oligonucleotide is used as a primer for PCR, the amplification mixture may include at least one nucleotide that is labeled with a quencher (e.g., Dabcyl). The labeled nucleotide may include at least one non-natural nucleotide. For example, the labeled nucleotide may include at least one nucleotide having a base that is not A, C, G, T, or U (e.g., iC or iG).

In some embodiments, the oligonucleotide may be designed not to form an intramolecular structure such as a hairpin. In other embodiments, the oligonucleotide may be designed to form an intramolecular structure such as a hairpin. For example, the oligonucleotide may be designed to form a hairpin structure that is altered after the oligonucleotide hybridizes to a target nucleic acid, and optionally, after the target nucleic acid is amplified using the oligonucleotide as a primer.

The oligonucleotide may be labeled with a fluorophore that exhibits quenching when incorporated in an amplified product as a primer. In other embodiments, the oligonucleotide may emit a detectable signal after the oligonucleotide is incorporated in an amplified product as a primer (e.g., inherently, or by fluorescence induction or fluorescence dequenching). Such primers are known in the art (e.g., LightCycler primers, Amplifluor® Primers, Scorpion® Primers and Lux™ Primers). The fluorophore used to label the oligonucleotide may emit a signal when intercalated in double-stranded nucleic acid. As such, the fluorophore may emit a signal after the oligonucleotide is used as a primer for amplifying the nucleic acid.

The oligonucleotides that are used in the disclosed methods may be suitable as primers for amplifying at least one nucleic acid in the sample and as probes for detecting at least one nucleic acid in the sample. In some embodiments, the oligonucleotides are labeled with at least one fluorescent dye, which may produce a detectable signal. The fluorescent dye may function as a fluorescence donor for fluorescence resonance energy transfer (FRET). The detectable signal may be quenched when the oligonucleotide is used to amplify a target nucleic acid. For example, the amplification mixture may include nucleotides that are labeled with a quencher for the detectable signal emitted by the fluorophore. Optionally, the oligonucleotides may be labeled with a second fluorescent dye or a quencher dye that may function as a fluorescence acceptor (e.g., for FRET). Where the oligonucleotide is labeled with a first fluorescent dye and a second fluorescent dye, a signal may be detected from the first fluorescent dye, the second fluorescent dye, or both. Signals may be detected at a gradient of temperatures (e.g., in order to determine a melting temperature for an amplicon or a complex that includes a probe hybridized to a target nucleic acid).

The disclosed methods may be performed with any suitable number of oligonucleotides. Where a plurality of oligonucleotides are used (e.g., two or more oligonucleotides), different oligonucleotide may be labeled with different fluorescent dyes capable of producing a detectable signal. In some embodiments, oligonucleotides are labeled with at least one of two different fluorescent dyes. In further embodiments, oligonucleotides are labeled with at least one of three different fluorescent dyes.

In some embodiments, each different fluorescent dye emits a signal that can be distinguished from a signal emitted by any other of the different fluorescent dyes that are used to label the oligonucleotides. For example, the different fluorescent dyes may have wavelength emission maximums all of which differ from each other by at least about 5 nm (preferably by least about 10 nm). In some embodiments, each different fluorescent dye is excited by different wavelength energies. For example, the different fluorescent dyes may have wavelength absorption maximums all of which differ from each other by at least about 5 nm (preferably by at least about 10 nm).

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. For example, the fluorescent dye for determining the melting temperature of a nucleic acid may have a wavelength emission maximum that differs from the wavelength emission maximum of any other fluorescent dye that is used for labeling an oligonucleotide by at least about 5 nm (preferably by least about 10 nm). In some embodiments, the fluorescent dye for determining the melting temperature of a nucleic acid may be excited by different wavelength energy than any other of the different fluorescent dyes that are used to label the oligonucleotides. For example, the fluorescent dye for determining the melting temperature of a nucleic acid may have a wavelength absorption maximum that differs from the wavelength absorption maximum of any fluorescent dye that is used for labeling an oligonucleotide by at least about 5 nm (preferably by least about 10 nm).

The methods may include determining the melting temperature of at least one nucleic acid in a sample (e.g., an amplicon or a nucleic acid complex that includes a probe hybridized to a target nucleic acid), which may be used to identify the nucleic acid. Determining the melting temperature may include exposing an amplicon or a nucleic acid complex to a temperature gradient and observing a detectable signal from a fluorophore. Optionally, where the oligonucleotides of the method are labeled with a first fluorescent dye, determining the melting temperature of the detected nucleic acid may include observing a signal from a second fluorescent dye that is different from the first fluorescent dye. In some embodiments, the second fluorescent dye for determining the melting temperature of the detected nucleic acid is an intercalating agent. Suitable intercalating agents may include, but are not limited to SYBR™ Green 1 dye, SYBR dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ Green 1 dye.

Typically, an intercalating agent used in the method will exhibit a change in fluorescence when intercalated in double-stranded nucleic acid. A change in fluorescence may include an increase in fluorescence intensity or a decrease in fluorescence intensity. For example, the intercalating agent may exhibit an increase in fluorescence when intercalated in double-stranded nucleic acid, and a decrease in fluorescence when the double-stranded nucleic acid is melted. A change in fluorescence may include a shift in fluorescence spectra (i.e., a shift to the left or a shift to the right in maximum absorbance wavelength or maximum emission wavelength). For example, the intercalating agent may emit a fluorescent signal of a first wavelength (e.g., green) when intercalated in double-stranded nucleic and emit a fluorescent signal of a second wavelength (e.g., red) when not intercalated in double-stranded nucleic acid. A change in fluorescence of an intercalating agent may be monitored at a gradient of temperatures to determine the melting temperature of the nucleic acid (where the intercalating agent exhibits a change in fluorescence when the nucleic acid melts).

In the disclosed methods, each of the amplified target nucleic acids may have different melting temperatures. For example, each of the amplified target nucleic acids may have a melting temperature that differs by at least about 1° C., more preferably by at least about 2° C., or even more preferably by at least about 4° C. from the melting temperature of any of the other amplified target nucleic acids.

The methods disclosed herein may include transcription of RNA to DNA (i.e., reverse transcription). For example, reverse transcription may be performed prior to amplification.

As used herein, "labels" or "reporter molecules" are chemical or biochemical moieties useful for labeling a nucleic acid, amino acid, or antibody. "Labels" and "reporter molecules" include fluorescent agents, chemiluminescent agents, chromogenic agents, quenching agents, radionuclides, enzymes, substrates, cofactors, scintillation agents, inhibitors, magnetic particles, and other moieties known in the art. "Labels" or "reporter molecules" are capable of generating a measurable signal and may be covalently or noncovalently joined to an oligonucleotide.

As used herein, a "fluorescent dye" or a "fluorophore" is a chemical group that can be excited by light to emit fluorescence. Some suitable fluorophores may be excited by light to emit phosphorescence. Dyes may include acceptor dyes that are capable of quenching a fluorescent signal from a fluorescent donor dye. Dyes that may be used in the disclosed methods include, but are not limited to, the following dyes and/or dyes sold under the following tradenames: 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DER (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DER); DiI (DiIC18(3)); Dinitrophenol; DiO (DiOC18(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; NED™; Nitrobenzoxadidole; Noradrenaline; Nuclear Fast Red; Nuclear Yellow; Nylosan Brilliant Iavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; TET™; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC TetramethylRodamineIsoThioCyanate; True Blue; TruRed; Ultralite; Uranine B; Uvitex SFC; VIC®; wt GFP; WW 781; X-Rhodamine; XRITC; Xylene Orange; Y66F; Y66H; Y66W; Yellow GFP; YFP; YO-PRO-1; YO-PRO-3; YOYO-1; YOYO-3; and salts thereof.

Fluorescent dyes or fluorophores may include derivatives that have been modified to facilitate conjugation to another reactive molecule. As such, fluorescent dyes or fluorophores may include amine-reactive derivatives such as isothiocyanate derivatives and/or succinimidyl ester derivatives of the fluorophore.

The oligonucleotides and nucleotides of the disclosed methods may be labeled with a quencher. Quenching may include dynamic quenching (e.g., by FRET), static quenching, or both. Suitable quenchers may include Dabcyl. Suitable quenchers may also include dark quenchers, which may include black hole quenchers sold under the tradename "BHQ" (e.g., BHQ-0, BHQ-1, BHQ-2, and BHQ-3, Biosearch Technologies, Novato, Calif.). Dark quenchers also may include quenchers sold under the tradename "QXL™" (Anaspec, San Jose, Calif.). Dark quenchers also may include DNP-type non-fluorophores that include a 2,4-dinitrophenyl group.

The oligonucleotide of the present methods may be labeled with a donor fluorophore and an acceptor fluorophore (or quencher dye) that are present in the oligonucleotides at positions that are suitable to permit FRET (or quenching). Labeled oligonucleotides that are suitable for the present methods may include but are not limited to oligonucleotides designed to function as LightCycler primers or probes, Taqman® Probes, Molecular Beacon Probes, Amplifluor® Primers, Scorpion® Primers, and Lux™ Primers.

In some embodiments, the detection of viruses that are capable of causing AIDS or AIDS-like symptoms may be performed using MultiCode®-RTx PCR technology, which is disclosed in U.S. Patent Application Publication No. 2002-0150900 and WO/01/90417 incorporated herein by reference in their entireties. The assays may be performed using real-time or continuous methods using any suitable commercial thermal cycler. The disclosed technology may be used to detect nucleic acid targets obtained from any source (e.g., human, animal and infectious disease samples).

ILLUSTRATIVE EMBODIMENTS

The following list of embodiments is illustrative with respect to the disclosed methods and kits.

Embodiment 1

A method of detecting a specific mutation in a heterogeneous population of polynucleotides, where the specific mutation, if present, is located in a first region of the population, and the population comprises one or more additional mutations located in a second region, the method comprising: (a) amplifying the population with a first set of primers to obtain an amplification product (e.g. which comprises the first region), where at least one primer of the first set of primers is capable of specifically hybridizing to the second region of the population; and (b) amplifying the product with a second set of primers to detect the mutation, where at least one primer of the second primer set includes at least one non-natural base.

Embodiment 2

The method of embodiment 1, where the at least one primer of the first primer set does not specifically hybridize to the first region of the population.

Embodiment 3

The method of embodiment 1, where the at least one primer of the second primer set specifically hybridizes to the first region of the population.

Embodiment 4

The method of embodiment 1, where the specific mutation comprises a single base change.

Embodiment 5

The method of embodiment 1, where the first region comprises a single nucleotide.

Embodiment 6

The method of embodiment 1, where at least one primer of the first set of primers includes at least one non-natural base.

Embodiment 7

The method of embodiment 1 or 6, where the at least one non-natural base is selected from iC and iG.

Embodiment 8

The method of embodiment 1, where the at least one primer of the second primer set which includes at least one non-natural base further comprise a label.

Embodiment 9

The method of embodiment 8, where the label is a fluorophore.

Embodiment 10

The method of embodiment 9, where amplifying the product with the second set of primers comprises, amplifying in the presence of at least one quencher coupled to a non-natural base.

Embodiment 11

The method of embodiment 1, where detecting the mutation comprise real-time detection.

Embodiment 12

The method of embodiment 1, where the population of polynucleotides comprises a sequence of HIV-1.

Embodiment 13

A method of detecting a specific mutation in a heterogeneous population of polynucleotides, where the specific mutation, if present, is located in a first region of the population and the population comprises one or more additional mutations located in a second region of the population, the method comprising: (a) reacting the population and a mixture of oligonucleotides, where the mixture comprises: (i) a first oligonucleotide capable of hybridizing to the first region of the population; and (ii) a pool of degenerate oligonucleotides capable of hybridizing to the second region of one or more polynucleotides of the population, where the first oligonucleotide and/or the pool comprises one or more non-natural bases and optionally a label; and (b) detecting the mutation.

Embodiment 14

The method of embodiment 1, where detecting comprises amplifying one or more polynucleotides of the population.

Embodiment 15

A method of detecting a specific mutation in a heterogeneous population of polynucleotides, where the specific mutation, if present, is located in a first region of the population and the population comprises one or more additional mutations located in a second region of the population, the method comprising: (a) reacting the population and a pool of degenerate oligonucleotides, where the oligonucleotides of the pool comprise one or more non-natural bases and where the pool comprises: (i) at least one oligonucleotide capable of hybridizing to the first region of one or more polynucleotides of the population; and (ii) a plurality of oligonucleotides capable of hybridizing to the second region of one or more polynucleotides of the population; and (b) detecting the mutation.

Embodiment 16

The method of embodiment 14 or 16, where the non-natural bases are selected from the group consisting of iso-G, iso-C and a combination thereof.

Embodiment 17

The method of embodiment 14 or 16, where the degenerate oligonucleotides further comprise at least one label.

Embodiment 18

The method of embodiment 14 or 16, where at least one label is a fluorophore.

Embodiment 19

The method of embodiment 14 or 16, where detecting comprises amplifying one or more polynucleotides of the population.

Embodiment 20

The method of embodiment 19, where detecting comprises amplifying one or more polynucleotides in the presence of one or more non-natural nucleotides.

Embodiment 21

The method of embodiment 14 or 16, where detecting comprises amplifying one or more polynucleotides of the population in the presence of at least one quencher coupled to a non-natural base.

Embodiment 22

The method of embodiment 21, where the non-natural base coupled to the at least one quencher is selected from the group consisting of iso-C and iso-G.

Embodiment 23

The method of embodiment 14 or 16, where detecting comprises real-time detection.

Embodiment 24

The method of embodiment 14 or 16, where the heterogeneous population of polynucleotides comprises a sequence of HIV-1.

Embodiment 25

A method for identifying HIV-1 in a sample comprising: (a) reacting a reaction mixture, the mixture comprising: (i) the sample; (ii) at least one oligonucleotide comprising at least one non-natural base, where the oligonucleotide is capable of specifically hybridizing to HIV-1 nucleic acid; and (b) detecting HIV-1 nucleic acid if present in the sample.

Embodiment 26

The method of embodiment 25, where the at least one oligonucleotide is selected from the group consisting of SEQ ID NOs:2-97.

Embodiment 27

A method of detecting the presence or absence of a mutation in a polynucleotide at a specific nucleotide, comprising amplifying the polynucleotide with primers to detect the presence or absence of the mutation, the primers comprising: (a) a first primer having a 3' nucleotide that is complementary to the specific nucleotide where the mutation is present and capable of amplifying the polynucleotide; (b) a second primer having a 3' nucleotide that is complementary to the specific nucleotide where the mutation is absent and capable of amplifying the polynucleotide; where the first primer and the second primer are not complementary to the polynucleotide at one or more positions other than the 3' nucleotide and do not include identical nucleotides at the one or more positions, and where at least one of the first primer and the second primer includes at least one non-natural base, which optionally, is present at the one or more positions.

Embodiment 28

The method of embodiment 27, where the first primer and the second primer are not complementary to the polynucleotide at a single position other than the 3' nucleotide and do not include identical nucleotides at the single position.

Embodiment 29

The method of embodiment 27, where at least one of the first primer and the second primer has a non-natural base at the one or more positions.

Embodiment 30

The method of embodiment 27, where both the first primer and the second primer have a non-natural base at the one or more positions.

Embodiment 31

The method of embodiment 27, where the non-natural base is selected from the group consisting of iso-G, iso-C and a combination thereof.

Embodiment 32

The method of embodiment 27, where at least one of the primers further comprises a label.

Embodiment 33

The method of embodiment 27, where each primer further comprises a label, and where each label is different.

Embodiment 34

The method of embodiment 27, where amplification comprises amplification in the presence of a quencher coupled to a non-natural base.

Embodiment 35

The method of embodiment 27, where detecting further comprises real-time detection.

Embodiment 36

The method of embodiment 27, where the polynucleotide comprises a sequence of HIV-1.

Examples

The diversity and utility of the methods and kits are demonstrated in the following examples which are meant to be instructive and not limiting.

A. Detection and Quantification of 20 Antiretroviral-Resistant HIV-1 Mutations

Twenty different mutations that result in antiretroviral-drug resistant HIV-1 were targeted for detection. All twenty mutations selected for study were in the pol region of the HIV-1 genome, and were located in either the reverse transcriptase gene or the protease gene. Table 1 lists the HIV-1 gene carrying the mutation, the amino acid change caused by the mutation, and the drug or drugs to which resistance is conferred. It is understood that the present methods may be used to detect other HIV sequences or mutations; the following examples are illustrative only and not meant to be limiting.

TABLE 1

HIV-1 Mutations that confer drug resistance

| Gene | Mutation | Drug(s) |
|---|---|---|
| reverse transcriptase ("RT") | M41L (TTG and CTG) | azidothymidine ("AZT") |
| RT | T215Y, T215F | AZT |
| RT | K65R | Didanosine ("DDI"); tenofovir ("TDF"); amdoxovir ("DAPD" or "AMDX") |
| RT | L74V | DDI; DAPD |
| RT | T69D | zalcitabine ("DDC") |
| RT | E44D | lamivudine ("3TC") |
| RT | V118I | 3TC |
| RT | M184V, M184I | 3TC; emtricitabine ("FTC") |
| RT | L100I | Multi-non-nucleoside reverse transcriptase inhibitors ("NNRTI") |
| RT | K103N | NNRTI |
| RT | Y181C, Y181I | NNRTI |
| RT | Y188L | NNRTI |
| protease | M46I | multi-drug resistance |
| protease | L90M | multi-drug resistance |
| protease | G48V | saquinavir |
| protease | D30N | nelfinavir |
| protease | I50V | aprenavir |

1. Target Preparation

HIV-1 sequences corresponding to by 2300-3285 of pNL4-3 (Genbank Accession No. M19921) were amplified from pNL4-3 plasmid DNA using standard PCR conditions. PCR products of 985 bp were cloned into pGEM-T vector (Promega, Madison, Wis.) using the T-A cloning method. Mutations were created using the Quik-Change mutagenesis kit (Stratagene, La Jolla, Calif.) according to manufacturer's instructions. Constructs and orientation were verified by DNA sequencing.

Plasmids were isolated using Plasmid Mini kits (QIAGEN, Valencia, Calif.). Plasmid concentration was determined by OD260 using an extinction coefficient of 50 µg/ml per OD (see e.g., Maniatis et al., Molecular Cloning. A Laboratory Manual. CSH Lab. N.Y. (1989)) and used as PCR targets and as templates for in vitro transcription. Plasmids were linearized immediately 3' of the HIV-1 insert using Sal I (New England Biolabs, Ipswich, Mass.). Following phenol extraction and ethanol precipitation, 1 µg of each linearized plasmid was transcribed into RNA using the Ampliscribe T7 Transcription Kit (Epicentre, Madison, Wis.) following the manufacturer's instructions. Transcription reactions were treated with RNAse-free DNAse to degrade plasmid template and then phenol extracted. Free nucleotides and pyrophosphate were removed by size exclusion chromatography using NAPS columns (Amersham, Piscataway, N.J.) following the manufacturer's instructions. Following lithium chloride ethanol precipitation, RNA was treated again with DNAse and then completely desalted with a second round of chromatography. RNA concentration was determined by OD260 and an extinction coefficient of 0.117 mM RNA nucleotide per OD. RNA and plasmid DNA targets were diluted in 10 mM MOPS pH 7.4, 0.1 mM EDTA.

2. Primer Design and Synthesis

Forward and reverse primers were designed to hybridize to the selected HIV-1 sequences in a background of plasmid pNL4-3 sequence (recombinant clone HIV-1 NY5/BRU (LAV-1) is cloned into pNL4-3; see Genbank #M19921). For each mutation, a wild-type and a mutant forward primer were designed. The wild-type and mutant forward primers for each target contained a different 5' label, either HEX (hexachlorofluresceín), FAM (6-carboxy-fluorescein) or CFO (CalFluor Orange). Primers were designed using Visual OMP software (DNA Software, MI) to have target specific Tm's of 50° C. (forward primer) and 60° C. (reverse primer).

The forward primers were constructed to have a 5' target-independent tail portion (e.g., non-complementary to the HIV sequence of interest). PCR reactions with tailed primers were performed as follows. A first round of PCR is performed at a lower temperature to allow the target specific region of the primers to hybridize. Extension with polymerase creates a new template with an extended primer binding site: the target specific sequences and the non-specific tail sequence. Due to the longer primer binding sites, subsequent rounds of hybridization may be performed at higher annealing temperatures. The higher annealing temperatures will likely decrease the amount of non-specific primer hybridization, thereby diminishing the amplification of undesired products.

Table 2 shows the primer sequences and labels used in the HIV-1 mutation detection reactions.

TABLE 2

Primer Sequences ("RTx primers")

| Protein | Site | Primers | Function | SEQ ID NO |
|---|---|---|---|---|
| Protease | 30N | CGCAGATTTCTATGAGTATCTGAT | Reverse (cDNA) | 2 |
| | | FAM(iC)GTTTAGCATACAGGAGCAGATG | WT Forward | 3 |

TABLE 2-continued

Primer Sequences ("RTx primers")

| Protein | Site | Primers | Function | SEQ ID NO |
|---|---|---|---|---|
| | | CFO(iC)GGCATGATACAGGAGCAGATA | MUT Forward | 4 |
| Protease | 46I | CTTCCAATTATGTTGACAGGTG | Reverse (cDNA) | 5 |
| | | FAM(iC)GAGCGATGGAAACCAAAAATG | WT Forward | 6 |
| | | CFO(iC)CCTGACATAGATGGAAACCAAAATA | MUT Forward | 7 |
| Protease | 48V | CTTCCAATTATGTTGACAGGTG | Reverse (cDNA) | 8 |
| | | FAM(iC)GTATCAACGAAACCAAAAATGATAGG | WT Forward | 9 |
| | | CFO(iC)CGTCCTGAAACCAAAAATGATAGT | MUT Forward | 10 |
| Protease | 50V | CTTCCAATTATGTTGACAGGTG | Reverse (cDNA) | 11 |
| | | FAM(iC)ACTGATGAAATGATAGGGGGAG | WT Forward | 12 |
| | | CFO(iC)ACTGCTAAAATGATAGGGGGAA | MUT Forward | 13 |
| Protease | 90M | GTACAAATTTCTACTAATGCTTTTATTTTT | Reverse (cDNA) | 14 |
| | | FAM(iC)CGACAATAAAATTGGAAGAAATCTGT | WT Forward | 15 |
| | | CFO(iC)CGCCATAATTGGAAGAAATCTGA | MUT Forward | 16 |
| RT | 41L-TTG | GCAAATACTGGAGTATTGTATGGA | Reverse (cDNA) | 17 |
| | | FAM(iC)CCATTTACTGTAGAAATTTGTACAGAAA | WT Forward | 18 |
| | | CFO(iC)GGCTGGTAGAAATTTGTACAGAAT | MUT Forward | 19 |
| RT | 41L-CTG | GCAAATACTGGAGTATTGTATGGA | Reverse (cDNA) | 20 |
| | | FAM(iC)CCATTTACTGTAGAAATTTGTACAGAAA | WT Forward | 21 |
| | | CFO(iC)GGTAAATGAGTAGAAATTTGTACAGAAC | MUT Forward | 22 |
| RT | 44D | ATTCCTAATTGAACTTCCCAGAAA | Reverse (cDNA) | 23 |
| | | FAM(iC)CTTGCTCAGAAATGGAAAGGAA | WT Forward | 24 |
| | | CFO(iC)CTGGATGAGAAATGGAAAGGAC | MUT Forward | 25 |
| RT | M184V (1) | CTCAACAGATGTTGTCTCAGTTCCTCTA | Reverse (cDNA) | 26 |
| | | FAM(iC)GACAGGAGACATAGTCATCTATCAATACA | WT Forward | 27 |
| | | HEXT(iC)TGTCCAATAGTCATCTATCAATACG | MUT Forward | 28 |
| RT | M184V (2) | TAAATCCCCACCTCAACAGAT | Reverse (cDNA) | 29 |
| | | FAM(iC)GAGTAAGCTAGTCATCTATCAATACATG | WT Forward | 30 |
| | | CFO(iC)CAGCCATAGTCATCTATCAATACG | MUT Forward | 31 |
| RT | 69D | GAAAAATATGCATCGCCCAC | Reverse (cDNA) | 32 |
| | | FAM(iC)TCGCTCATAAAGAAAAAGACAGTA | WT Forward | 33 |
| | | CFO(iC)CGGTTCATAAAGAAAAAGACAGTC | MUT Forward | 34 |
| RT | 74V | CATCGCCCACATCCAG | Reverse (cDNA) | 35 |

TABLE 2-continued

Primer Sequences ("RTx primers")

| Protein | Site | Primers | Function | SEQ ID NO |
|---|---|---|---|---|
| | | FAM(iC)GCTACGAGTACTAAATGGAGAAAAT | WT Forward | 36 |
| | | CFO(iC)CCCTGTGTACTAAATGGAGAAAG | MUT Forward | 37 |
| RT | 100L | CCCTGGTGTCTCATTGTTT | Reverse (cDNA) | 38 |
| | | FAM(iC)TGTTGAAATCCTGCAGGGT | WT Forward | 39 |
| | | CFO(iC)AGACGATCCTGCAGGGA | MUT Forward | 40 |
| RT | 103N | CCCTGGTGTCTCATTGTTT | Reverse (cDNA) | 41 |
| | | FAM(iC)AGGACCCAGGGTTAAAACAGAAA | WT Forward | 42 |
| | | CFO(iC)GTCTCGAGGGTTAAAACAGAAC | MUT Forward | 43 |
| RT | 118I | TGTCATGCTACACTGGAATATTG | Reverse (cDNA) | 44 |
| | | FAM(iC)TGCCCGATGCATATTTTTCAG | WT Forward | 45 |
| | | CFO(iC)TCCGTCGATGCATATTTTTCAA | MUT Forward | 46 |
| RT | 181C | TAAATCCCCACCTCAACAGAT | Reverse (cDNA) | 47 |
| | | FAM(iC)CCGTTCCAGACATAGTCATCTA | WT Forward | 48 |
| | | CFO(iC)AGGCACAGACATAGTCATCTG | MUT Forward | 49 |
| T | 181I | TAAATCCCCACCTCAACAGAT | Reverse (cDNA) | 50 |
| | | FAM(iC)CCGTTCCAGACATAGTCATCTA | WT Forward | 51 |
| | | CFO(iC)GGTTAGTCCAGACATAGTCATCA | MUT Forward | 52 |
| RT | M184I | TAAATCCCCACCTCAACAGAT | Reverse (cDNA) | 53 |
| | | FAM(iC)GAGTAAGCTAGTCATCTATCAATACATG | WT Forward | 54 |
| | | CFO(iC)CATTCGCATAGTCATCTATCAATACATA | MUT Forward | 55 |
| RT | K65R (1) | ACCCTGCAGGATGTGG | Reverse (cDNA) | 56 |
| | | FAM(iC)ACAGGTAGTATTTGCCATAAAGAA | WT Forward | 57 |
| | | CFO(iC)GACATCGTATTTGCCATAAAGAG | MUT Forward | 58 |
| RT | K65R (2) | CTGATTTTTTCTGTTTTAACCCTGC | Reverse (cDNA) | 59 |
| | | FAM(iC)TCACGTAGTATTTGCCATAAAGAA | WT Forward | 60 |
| | | CFO(iC)TGCTGGTATTTGCCATAAAGAG | MUT Forward | 61 |
| RT | 188L- | CTTAAGGAATGGAGGTTCTTTCTG | Reverse (cDNA) | 62 |
| | | FAM(iC)GACGGTAATACATGGATGATTTGTA | WT Forward | 63 |
| | | CFO(iC)GCCTAAGACATGGATGATTTGC | MUT Forward | 64 |
| RT | 188L- | TTAAGGAATGGAGGTTCTTTCTG | Reverse (cDNA) | 65 |
| | | FAM(iC)GACGGTAATACATGGATGATTTGTA | WT Forward | 66 |
| | | CFO(iC)CCGCTATACATGGATGATTTGTT | MUT Forward | 67 |

TABLE 2-continued

Primer Sequences ("RTx primers")

| Protein | Site | Primers | Function | SEQ ID NO |
|---|---|---|---|---|
| RT | 215F | AGCACTATAGGCTGTACTGTC | Reverse (cDNA) | 68 |
|  |  | FAM(iC)ATCTGTTTGAGGTGGGGATTTA | WT Forward | 69 |
|  |  | CFO(iC)TGTGAGAGGTGGGGATTTTT | MUT Forward | 70 |
| RT | 215Y | AGCACTATAGGCTGTACTGTC | Reverse (cDNA) | 71 |
|  |  | FAM(iC)ATCTGTTTGAGGTGGGGATTTA | WT Forward | 72 |
|  |  | CFO(iC)CTAGACAGAGGTGGGGATTTTA | MUT Forward | 73 |

3. General Reaction and Cycling Conditions

For each assay, PCR primers were used at the following concentrations. Each reaction received 200 nM of a wild-type forward primer and 200 nM of a mutant forward primer. The M184V mutant primer was used at 150 nM; the K65K (wild-type) and K65R (mutant) primers were used at 100 nM. A single reverse primer was used for each system at 400 nM.

Either 100 or 1000 copies of mutant RNA or DNA with 10-fold dilution series of wild-type targets (DNA or RNA) from 0 to $10^6$ targets were tested with each primer set.

PCR conditions were as follows: 25 uL reactions in 1× ISOlution buffer (EraGen, Madison, Wis.) and Titanium Taq DNA polymerase (Clontech, Mountain View, Calif.) at manufacturers recommended concentration. For RT-PCR assays the conditions included the following: 0.5 Units/uL Maloney Murine Reverse Transcriptase (M-MLV RT) and 5 mM dithiothreitol and an additional 5 minutes at 50° C. added prior to the denaturation step.

Cycling parameters for reactions performed on the ABI 7900 (Applied Biosystems, Foster City, Calif.) real-time thermal cycler were as follows:

2 minutes denature at 95° C., 1 cycle of 5 sec at 95° C., 5 sec at 45° C., 20 sec at 72° C., followed by 45 cycles of 5 sec at 95° C., 5 sec at 60° C., 20 sec at 72° C. with optical read. A thermal melt at 7% ramp rate with optical read from 60 to 95° C. was performed directly following the last 72° C. step of thermal cycling.

Cycling parameters for reactions performed on the Roche LightCycler (Roche, Indianapolis, Ind.) were as follows unless otherwise specified:

2 minutes denature at 95° C., 1 cycle of 1 sec at 95° C., 1 sec at 45° C., 1° C./sec ramp to 20 sec at 72° C., followed by 50 cycles of 5 sec at 95° C., 5 sec at 55° C., 1° C./sec ramp to 20 sec at 72° C. (SINGLE read), melt 60-95° C. 0.4° C./sec ramp; (STEP read).

Cycle threshold data was analyzed to determine the sensitivity of each system for both mutant and wild-type as determined by the lowest copy number of targets that could consistently be detected. The slope of each wild-type standard curve was also determined as a measure of PCR efficiency.

B. Detection of HIV-1 Mutations in RNA Targets on the ABI 7900

HIV-1 drug resistant mutant RNA targets were mixed at 100 or 1000 copies with wild-type RNA target in a 10-fold dilution series from 0 to $10^6$ copies. Assays were performed using the ABI 7900. Targets were amplified using the cycling parameters described above. Cycle threshold data was analyzed to determine the sensitivity of each system for both mutant and wild-type as shown by the lowest copy number of targets that could consistently be detected. The slope of each wild-type standard curve was also determined as a measure of PCR efficiency.

Results are shown in Table 3. Sensitivity to both wild-type and mutant targets in copy numbers is presented; "not detected" indicates sensitivity greater than 1000 mutant RNA targets. The "Best Mixture" is the lowest percentage mutant target in a mixture with wild-type target that could be detected. "Slope" is the slope wild-type standard curve in log copy number vs. cycle threshold. A slope of −0.32 indicates 100% PCR efficiency with greater values indicating reduced PCR efficiency. "RT" indicates HIV-1 reverse transcriptase. Numerous systems can detect 100 copies of both wild-type and mutant RNA in a mixture of 1% or less.

TABLE 3

RNA detection results

| | | Wild-type | | Mutant | |
|---|---|---|---|---|---|
| Protein | Site | Sensitivity | Slope | Sensitivity | Best Mixture |
| protease | 30N | 10 | −0.23 | 100 | 0.1% |
| protease | 46I | 10000 | −0.25 | Not detected | MUT Fails |
| protease | 48V | 100000 | −0.25 | 1000 | 0.1% |
| protease | 50V | 100 | −0.24 | 100 | 0.1% |
| protease | 90M | 10000 | −0.27 | 1000 | 0.1% |
| RT | 41L-CTG | 100 | −0.22 | 100 | 0.01% |
| RT | 44D | 10 | −0.23 | 100 | 0.01% |
| RT | 65R (1) | 100 | −0.26 | 100 | 0.1% |
| RT | 65R (2) | 10 | −0.22 | 100 | 0.01% |
| RT | 69D | 1000 | −0.19 | Not detected | MUT Fails |
| RT | 74V | 10000 | −0.22 | 100 | 1% |
| RT | 103N | 10000 | −0.25 | 100 | 1% |
| RT | 118I | 10000 | −0.32 | 1000 | MUT Fails |
| RT | 181C | 10 | −0.23 | Not detected | MUT Fails |
| RT | 181I | 10 | −0.28 | 100 | 0.01% |
| RT | 184I | 100 | −0.24 | 100 | 0.01% |
| RT | 184V (1) | 10 | −0.24 | 100 | 0.01% |
| RT | 184V (2) | 10 | −0.23 | 100 | 0.01% |
| RT | 188L-CTT | 10 | −0.23 | 100 | 0.1% |
| RT | 188L-TTA | 10 | −0.23 | 1000 | 0.1% |
| RT | 215F | 10 | −0.22 | 100 | 1% |
| RT | 215Y | 10 | −0.26 | 100 | 1% |

C. Detection of HIV-1 Mutations in DNA Targets on the ABI 7900 and the LightCycler HIV-1 drug resistant mutant plasmid DNA clone targets were mixed at 100 or 1000 copies with wild-type DNA target in a 10-fold dilution series from 0 to $10^6$ copies. Assays were performed on the ABI 7900 and the Roche LightCycler (Roche, Indianapolis, Ind.) using cycling parameters described above in section A.3.

Cycle threshold data was analyzed to determine the sensitivity of each system for both mutant and wild-type as shown by the lowest copy number of targets that could consistently be detected. The slope of each wild-type standard curve was also determined as a measure of PCR efficiency.

Results are presented in Tables 4A and B. "Sensitivity" to both wild-type and mutant targets in presented as copy number. "Not detected" indicates a sensitivity greater than 1000 mutant RNA targets. "Best Mixture" is the lowest percentage mutant target in a mixture with wild-type target that was detected.

"Slope" is the slope wild-type standard curve in log copy number vs. cycle threshold. A slope of −0.32 indicates 100% PCR efficiency with greater values indicating reduced PCR efficiency. "RT" indicates reverse transcriptase. Again, numerous systems can detect 100 copies of both wild-type and mutant RNA in a mixture of 1% or less on either the ABI or the LightCycler. Note that two independent systems for the 65R and the 184V loci were evaluated.

TABLE 4A

DNA Detection Results

ABI 7900

| Protein | Site | Wild-type Sensitivity | Slope | Mutant Sensitivity | Best Mixture |
|---|---|---|---|---|---|
| protease | 30N | 10 | −0.29 | 1000 | 0.1% |
| protease | 46I | 10 | −0.24 | 100 | 0.1% |
| protease | 48V | 100 | −0.23 | 100 | 0.01% |
| protease | 50V | 1000 | −0.24 | 1000 | 50% |
| protease | 90M | 100000 | −0.17 | Not detected | MUT Fails |
| RT | 41L-TTG | 100 | −0.22 | 100 | 0.01% |
| RT | 41L-CTG | 100 | −0.22 | 100 | 0.01% |
| RT | 44D | 1000 | −0.21 | 1000 | 90% |
| RT | 65R (1) | 100 | −0.28 | 100 | 0.01% |
| RT | 65R (2) | 10 | −0.23 | 100 | 0.01% |
| RT | 69D | 100 | −0.24 | 1000 | 0.01% |
| RT | 74V | 100 | −0.27 | 100 | 0.1% |
| RT | 100L | 10000 | −0.24 | 1000 | 0.1% |
| RT | 103N | 100 | −0.24 | 100 | 0.1% |
| RT | 118I | 100 | −0.26 | 100 | 50% |
| RT | 181C | 10 | −0.23 | Not detected | MUT Fails |
| RT | 181I | 100 | −0.26 | Not detected | MUT Fails |
| RT | 184I | 100 | −0.24 | 100 | 0.01% |
| RT | 184V (1) | 1000 | −0.25 | 1000 | 0.1% |
| RT | 184V (2) | 1000 | −0.24 | 1000 | 0.1% |
| RT | 188L-CTT | 10 | −0.24 | 1000 | 10% |
| RT | 188L-TTA | 100 | −0.22 | 100 | 0.1% |
| RT | 215F | 10 | −0.27 | 100 | 0.01% |
| RT | 215Y | 10 | −0.26 | 100 | 1% |

TABLE 4B

DNA Detection Results

Light Cycler

| Protein | Site | Wild-type Sensitivity | Slope | Mutant Sensitivity | Best Mixture |
|---|---|---|---|---|---|
| protease | 30N | 1000 | −0.14 | 1000 | 0.1% |
| protease | 46I | 10 | −0.12 | 100 | 0.01% |
| protease | 48V | 100 | −0.09 | 100 | 0.01% |
| protease | 50V | 100 | −0.16 | 1000 | 90% |
| protease | 90M | 1000 | −0.08 | 100 | 0.1% |
| RT | 41L-TTG | 1000 | −0.12 | 100 | 0.01% |
| RT | 41L-CTG | 10000 | −0.09 | 100 | 0.01% |

TABLE 4B-continued

DNA Detection Results

Light Cycler

| Protein | Site | Wild-type Sensitivity | Slope | Mutant Sensitivity | Best Mixture |
|---|---|---|---|---|---|
| RT | 44D | 100 | −0.09 | 100 | 0.1% |
| RT | 65R (1) | 100 | −0.22 | 100 | 0.1% |
| RT | 65R (2) | 100 | −0.08 | 100 | 0.01% |
| RT | 69D | 100 | −0.08 | 100 | 0.01% |
| RT | 74V | 1000 | −0.18 | 100 | 0.01% |
| RT | 100L | 1000 | −0.15 | 100 | 0.01% |
| RT | 103N | 100 | −0.16 | 100 | 0.1% |
| RT | 118I | 10 | −0.12 | 1000 | 0.1% |
| RT | 181C | 1000 | −0.12 | Not detected | MUT Fails |
| RT | 181I | 100 | −0.20 | 100 | 90% |
| RT | 184I | 100 | −0.09 | 100 | 0.01% |
| RT | 184V (1) | 10 | −0.23 | 1000 | 0.1% |
| RT | 184V (2) | 1000 | −0.15 | 1000 | 0.1% |
| RT | 188L-CTT | 1000 | −0.16 | 100 | 0.01% |
| RT | 188L-TTA | 100 | −0.14 | 100 | 0.01% |
| RT | 215F | 100 | −0.12 | 100 | 0.01% |
| RT | 215Y | 10 | −0.14 | 100 | 0.01% |

D. Detection of M184V and K65R in DNA Targets Using Different Cycling Parameters and Different Instruments To test for cycling robustness, the M184V and K65R assays were run and tested using the ABI 7900 instrument and the cycling parameters described in section A.3, and the Roche LightCycler using the three different sets of cycling parameters, with ramp rates of 20° C./sec (unless otherwise specified), described below.

1) 2 minute denature at 95° C., 1 cycle of 1 sec at 95° C., 1 sec at 45° C., 1° C./sec ramp to 20 sec at 72° C., 50 cycles 5 sec at 95° C., 5 sec at 55° C., 1° C./sec ramp to 20 sec at 72° C. (SINGLE read), melt 60-95° C. 0.4° C./sec ramp; (STEP read);
2) 2 min denature at 95° C., 1 cycle of 1 sec at 95° C., 1 sec at 45° C., 20 sec at 72° C., 50 cycles of 5 sec at 95° C., 5 sec at 55° C., 1° C./sec ramp to 20 sec at 72° C. (SINGLE read), melt 60-95° C. 0.4° C./sec ramp (STEP read);
3) 2 minute denature at 95° C., 1 cycle of 1 sec at 95° C., 1 sec at 45° C., 20 s at 72° C., 100 cycles of 1 sec at 95° C., 1 sec at 55° C., to 20 sec at 72° C. (SINGLE read), melt 60-95° C. 0.4° C./sec ramp (STEP read).

Mixtures of wild-type and mutant cloned DNA targets were prepared containing $10^3$ to $10^7$ copies of mutant or wild-type targets at 10-fold intervals, with a total of $10^7$ copies per reaction. This provided mixtures that varied in wild-type and mutant targets from 0.01 to 100%.

Linear regression analysis was performed to determine log [copy number] vs. $C_t$ for the individual channels. Each condition for M184 afforded tight $r^2$ values which varied from 0.991 to 0.998 for the wild-type M184M channel and 0.990 to 0.997 for the mutant M184V channel. Linear regression for the K65 system had $r^2$ values which varied from 0.949 to 0.955 for the wild-type K65K channel and 0.977 to 0.994 for the mutant K65R channel. By measuring the differences between the $C_t$ channels of wild-type and mutant ($C_t$ of the mutant minus the $C_t$ of the wild-type, defined as $\Delta C_t$) $\Delta C_t$ standard curves were established for each condition. These standard curves may be used to determine the make-up of unknown sample mixtures.

Results are shown in FIGS. 3A and 3B, which shows AC, vs. fraction mutant plots for real-time PCR with the four different cycling conditions. "Fraction Mut" is the fraction of mutant DNA template in a mixture with wild-type DNA, with fractions detected down to 1 in 10,000 copies (0.0001). A1-A4 show the curves for K65V detection and B1-B4 show the curves for M184V detection. A1-A3 and B1-B3 were performed on the Roche LightCycler, and A4 and B4 were performed on the ABI 7900.

E. Detection of Mutations Using Varied Concentrations of RNA Targets

Figure 4:
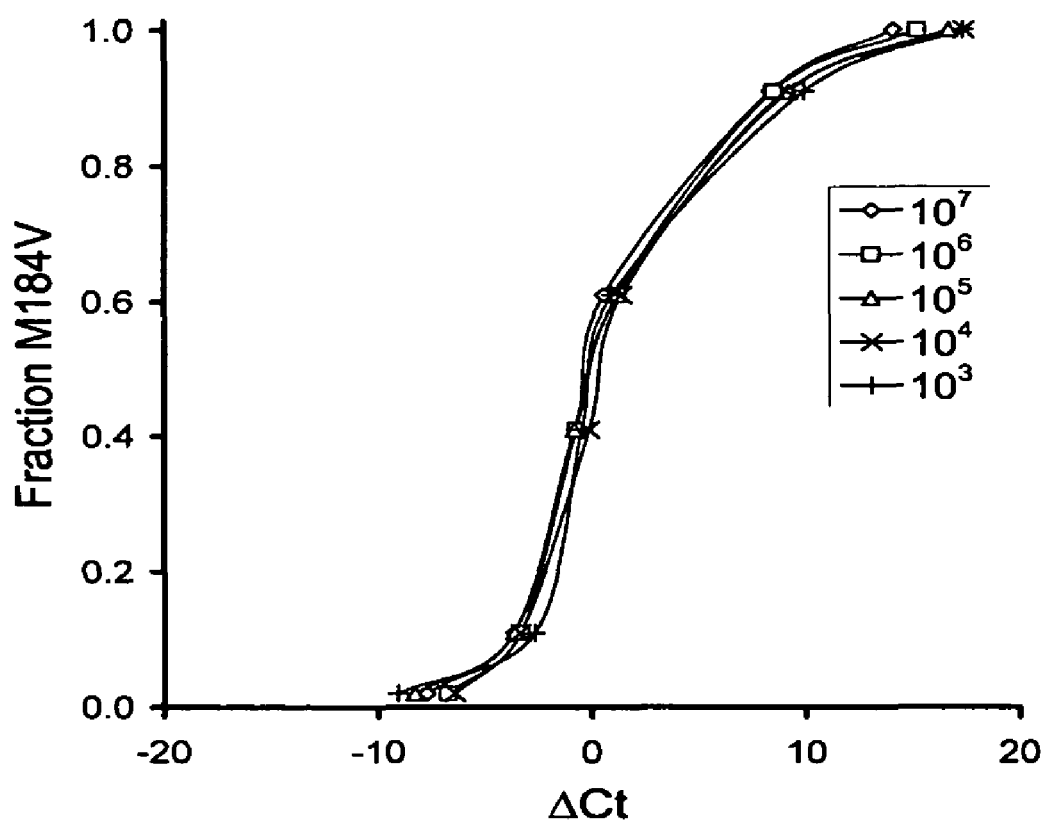
FIG. 4 shows $\Delta C_t$ analysis of different total concentration fraction series.

RNA target mixtures were diluted in a 10-fold series from $10^3$ to $10^7$ total copies, using mixtures of targets from 1% to 99% M184V. Reactions were performed on the ABI 7900 as described in section A.3. ΔCt values were determined for each sample and then plotted vs. fraction M184V in the mixtures. These different curves were then overlaid, and are shown in FIG. 4. The results indicate that the detection methods allowed for percentages to be determined even as the overall concentration changes over four orders of magnitude (four logs of total viral particle input did not affect the overall curve). Accordingly, the method may be used to discriminate mixed populations even through a large range in overall concentration. Thus, quantification of the mixed viral populations need not be determined prior to mixed population analysis.

F. Detection of M184M, M184V and M184I DNA on Light-Cycler Using Triplex Detection System Two different drug resistant mutants at codon 184 in the reverse transcriptase gene have been identified, M184V and M184I. Both are the result of transition mutations. In the case of M184V, the wild-type codon ATG, which codes for methionine becomes mutant GTG which codes for valine. In the case of the M184I mutant, the wild-type codon ATG becomes mutant ATA which codes for isoleucine.

Primers used for the detection of the three different alleles were labeled with three different fluorophores. The primers for the three different detection systems were combined in the reaction along with quenchers capable of quenching the different fluorophores. Five different targets mixes (containing $2\times10^6$ total copies) were tested: 100% M184M; 100% M184V; 100% M184I; 50% M184I: 50% M184M; 50% M184V: 50% M184M. Reactions were performed on the Roche LightCycler, using cycling parameters described in section A.3. Real-time and PCR melt data confirmed that such a triplex system is capable of detecting specific mutations in a mixed population. Probes specific for the M184M targets detected these targets in the 100% M184M mix, the 50% M184I: 50% M184M mix, and in the 50% M184I: 50% M184M mix. Probes specific for the M184V targets detected these targets in the 10% M184V mix and the 50% M184V: 50% M184M mix. Probes specific for the M184I targets detected these targets in the 100% M184I and the 50% M184I: 50% M184M mix.

G. Detection of HIV-1 Drug Resistant Mutants from Patient Samples

To further assess the detection methods, viral RNA extracted from 13 serum samples containing HIV-1 which had previously been genotyped by the line probe assay (LiPA) was tested. These samples were obtained from subjects undergoing non-nucleoside reverse transcriptase inhibitor ("NRTI") therapy between the years 1994 and 1997 and displaying M184M, M184V or a mixed population of M and V by LiPA. The extracted RNA was tested in duplicate using the M184V system as described above using ABI 7900 and cycling parameters described above in A.3. Table 5 indicates that the detection methods were able to amplify and genotype all samples. The results from ten of the samples were completely concordant with LiPA. Of the three samples that were not 100% concordant (samples 2, 4 and 11), two samples displayed a mixture of M and V where LiPA only detected V (samples 4 and 11). For the third sample, the opposite was true; the present detection methods showed 100% M while LiPA displayed a mixture (sample 2). The range of allele fractions from the samples were tested at least twice in independent real-time PCR experiments (HIV Monitor, Roche, Indianapolis, Ind.) and compared to previous results determined by LiPA.

TABLE 5

Viral genotypes and load

| LIPA[a] | RTx | Viral Load/ml[b] | Bleed Date | Sample |
|---|---|---|---|---|
| 184M | 100% M | $6.5 \times 10^5$ | Dec. 15, 1994 | 1 |
| 184M/V | 100% M | ND | Feb. 27, 1995 | 2 |
| 184M | 100% M | $1.7 \times 10^5$ | Nov. 03, 1996 | 3 |
| 184V | 64-92% V | $1.6 \times 10^4$ | Aug. 23, 1996 | 4 |
| 184V | 100% V | $1.4 \times 10^6$ | Jun. 21, 1996 | 5 |
| 184M | 100% M | $1.1 \times 10^6$ | Feb. 15, 1996 | 6 |
| 184M | 100% M | $1.8 \times 10^5$ | Jun. 08, 1995 | 7 |
| 184V | 100% V | $2.8 \times 10^5$ | Jun. 21, 1997 | 8 |
| 184M | 100% M | $1.2 \times 10^5$ | Nov. 16, 1995 | 9 |
| 184V | 100% V | $1.0 \times 10^5$ | Apr. 26, 1996 | 10 |
| 184V | 90-100% V | $4.3 \times 10^5$ | Jun. 28, 1996 | 11 |
| 184M | 100% M | $3.3 \times 10^5$ | Dec. 29, 1995 | 12[c] |
| 184V | 100% V | $1.6 \times 10^5$ | Jun. 28, 1996 | 13[c] |

[b]viral load determined via Roche Monitor ™ system.
[c]Samples only tested once.

H. Detection of Mutations in 13 HIV-1 Viral Clones Using Degenerate Primers

Plasmid DNA of 13 clones from the NIH Multidrug Resistant HIV-1 Reverse Transcriptase Panel and a wild-type clone (i.e., no M184 mutation, pNL4-3 was used) were tested using the M184V assay. Numerous background polymorphisms exist within these clones, and the assay results indicated less than 50% of the clones could be genotyped. Table 6.

To evaluate the extent of the polymorphisms present in the clones, the sequences of the discriminatory primers for each system were aligned with the sequences of the clones to determine the number of mismatched bases between the primer and different clone template sequences. The total number of mismatches was divided by the number of calls made to determine the average number of primer-target mismatches for both primers.

TABLE 6

Detection of M184V Viral Clones with Standard Primers

| | Calls | | | Average Mismatches per Clone | | |
|---|---|---|---|---|---|---|
| Mutation | Correct | Not Called | Miscalled | Correct | Not Called | Miscalled |
| M184V | 6 | 7 | 0 | 2.8 | 5.4 | NA |

Notably, there were no incorrect calls for this system. It was also noted that when the number of mismatches increased, so did the inability to genotype.

I. Use of Degenerate Primers to Detect HIV-1 Mutations

Degenerate primers for the detection of the M184V mutation were synthesized as a pool using mixed phosphoramidites to insert multiple bases that corresponded to the most common substitutions in HIV-1 clades B, C, and E. Using the NIH panel plasmid clones described above, the RTx degenerate primers were evaluated using reaction conditions described in section A, above, and the ABI 7900 with the following cycling parameters:

2 minute denature at 95° C., followed by one cycle of 5 s at 95° C., 30 s at 40° C., 20 s at 72° C., followed by 60 cycles of 5 s at 95° C., 5 s at 50° C., 20 s at 72° C., melt 60° C. to 95° C. 7% ramp.

The results of the primer redesign are shown in Table 7 below. Bolding of letters within sequences indicates differences between targets, degenerate primer sequence and pNL4-3; R=A or G base, Y=C or T base. Note that the primer pairs are labeled with separate fluorophores. The sequence for each target within the priming region is shown, along with the Tm for both the forward and reverse non-degenerate primer. The results are shown on the right. Black, filled columns A-B indicate that the correct genotype was obtained in the detection reactions. Reactions: A, standard (non-degenerate) primers and 2×10⁶ copies target used; B, degenerate primers and 2×10⁶ copies of target DNA used. "For.Tm" is the predicted melting temperature in ° C. of the forward primer including complementary 3' base on template under reaction conditions. "Rev. Tm" is the predicted melting temperature in ° C. of the reverse primer (sequence not shown) on template under reaction conditions; bold indicates lowest reverse primer Tm on samples tested.

Again, the standard primers genotyped 6 of 13 subject-derived clones (Column A). It was noted the $T_m$ of the forward primer for the targets not genotyped was very low. Reactions using degenerate primers amplified and correctly genotyped 11 of the 13 clones (Column B). Additional clone 12-21 was isolated by cloning of cDNA from an HIV-1 infected subject sample for this study.

the wild-type "T". The M184V forward primer has the sequence 5'-HEXT(iC)TGTCCAATAGTCATCTAT-CAATACG (SEQ ID NO: 28), where the 3' "G" hybridizes to the mutant "C".

The sequence alignment of the 13 clones in Table 7 shows a polymorphism adjacent to M184 A/G mutation site. Some clones show a "T" while other show a "C" at this position. Primers were designed with a mismatch at this position having the following sequences. The forward mismatch primer specific for M184M is as follows: HEX(iC)GACAGGAGA-CATAGTTATCTATCAATATA (SEQ ID NO: 76). The forward mismatch primer specific for M184V is as follows:

(SEQ ID NO: 77)
FAM(iC)TGTCCAGACATAGTTATCTATCAATAGG.

Note that for the M184M forward primer, the "T" adjacent to the 3' end will not match either the "T" or the "C" in the any of the target sequences. Similarly, the "G" adjacent to the 3' end of the M184V primer will not match either the "C" or the "T" in any of the target sequences. In addition to the mismatch primers described above, the following non-mismatch primers were also tested:

(SEQ ID NO: 78)
5'-HEX(iC)GACAGGAGACATAGTTATCTATCAATACA,
and

TABLE 7

Exemplary M184 Primer re-design

| Degenerate Primers | | GACATRGTYATCTATCARTAYR | SEQ IN NO 74 | | | |
|---|---|---|---|---|---|---|
| Standard Primers | | GACATAGTCATCTATCAATACR | SEQ ID NO 75 | | Reaction | |
| Sample | SEQ ID NO: | Sequence | For. Tm | Rev. Tm | A | B |
| pNL4-3 | 98 | GACATAGTCATCTATCAATACA | 54.2 | 65.4 | | |
| 7324-1 | 99 | GAAATAGTTATCTATCAATATA | 28.5 | 59.5 | | |
| 7324-4 | 100 | GAAATAGTTATCTATCAATATA | 28.5 | 59.5 | | |
| 10076-4 | 101 | GAAATGGTTATCTATCAATACG | 26.8 | 65.4 | | |
| 7295-1 | 102 | GACATAGTCATCTATCAATACG | 55.4 | 61.2 | | |
| 4755-1 | 103 | GACATAGTTATCTATCAATATG | 40.7 | 51.9 | | |
| 6463-13 | 104 | GAAATAGTTATCTATCAATACG | 37.3 | 43.4 | | |
| 7303-3 | 105 | GACATAGTTATCTATCAATACA | 45.5 | 43.4 | | |
| 1617-1 | 106 | GACATGGTTATCTATCAATATG | 30.6 | 65.1 | | |
| 35764-2 | 107 | GACATAGTTATCTATCAATACA | 45.5 | 61.5 | | |
| 29129-2 | 108 | GATATAGTCATCTATCAATACG | 47.8 | 48.6 | | |
| 52534-2 | 109 | GACATAGTTATCTATCAATACG | 47.0 | 61.9 | | |
| 56252-1 | 110 | GACATAGTTATCTATCAATACA | 45.5 | 65.4 | | |
| 12-21 | 111 | GACATAGTTATTTACCAATACA | 25.8 | 65.1 | | |

J. Incorporating Mismatches into Primer Sequences

RTx primers were designed with specific mismatches. In one embodiment, the mismatches were positioned adjacent to the 3' base of the forward RTx primer. As previously described, two different forward primers may be used in the RTx reactions. One forward primer has a 3' base that will hybridize to the wild-type nucleotide sequence of the target, while the other primer has a 3' base that will hybridize to the mutant nucleotide sequence of the target. For example, one of the M184M forward primers described in Table 2 has the sequence 5'-FAMT(iC)GACAGGAGACATAGTCATCTAT-CAATACA (SEQ ID NO: 27), where the 3' "A" hybridizes to -continued (SEQ ID NO: 79)
5'-FAM(iC)TGTCCAGACATAGTTATCTATCAATACG.

Reactions were prepared as follows: all odd numbered samples contained M184M target and all even numbered samples contained M184V target. Samples 1 and 2 contained both non-mismatched primers; samples 3 and 4 contained the mismatched M184M primer and the non-mismatched M184V primer; samples 5 and 6 contained the mismatched M184V primer and the non-mismatched M184M primer;

samples 7 and 8 contained both the mismatched M184M and the M184V primers. PCR cycling conditions were as follows:

15 m at 54° C., 2 minutes at 95° C., followed by 3 cycles of 5 s at 95° C., 5 s at 61° C., 1° C./sec, 10 s at 72° C., followed by 1 cycle of 5 s at 95° C., 5 s at 45° C., 1° C./sec 20 s at 72° C.)1, followed by 110 cycles of (5 s at 95° C., 5 s at 55° C., 20 s at 72° C.), melt 60° C. to 95° C. 0.4° C. STEP.

Real-time results demonstrate improved discrimination when both mismatched primers are used as compared to both non-mismatch or only one mismatch (data not shown).

K. Primer Mismatches Using Non-Natural Nucleotides

RTx primers with mismatches were designed with non-natural nucleotides, here either iso-G or iso-C, in the mismatch position. Using the HIV-1 M184 sequence as target, the primers designed and tested are shown in Table 8 below.

TABLE 8

| SEQ ID NO: | PRIMER SEQUENCE | TARGET |
|---|---|---|
| 80 | HEX-XGACAGGAGACATAGTTATCTATCAATACA | HIV M184M |
| 81 | FAM-XTGTCCAGACATAGTTATCTATCAATACG | HIV M184V |
| 82 | HEX-XGACAGGAGACATAGTTATCTATCAATAXA | HIV M184M |
| 83 | FAM-XTGTCCAGACATAGTTATCTATCAATAXG | HIV M184V |
| 84 | HEX-XGACAGGAGACATAGTTATCTATCAATAYA | HIV M184M |
| 85 | FAM-XTGTCCAGACATAGTTATCTATCAATAGY | HIV M184V |
| 86 | HEX-XGACAGGAGACATAGTTATCTATCAATYCA | HIV M184M |
| 87 | FAM-XTGTCCAGACATAGTTATCTATCAATYCG | HIV M184V |
| 88 | HEX-XGACAGGAGACATAGTTATCTATCYATACA | HIV M184M |
| 89 | FAM-XTGTCCAGACATAGTTATCTATCYATACG | HIV M184V |
| 90 | HEX-XGACAGGAGACATAGTTATCTYTCAATYCA | HIV M184M |
| 91 | FAM-XTGTCCAGACATAGTTATCTYTCAATYCG | HIV M184V |
| 92 | HEX-XGACAGGAGACATAGTTYTCTATCYATACA | HIV M184M |
| 93 | FAM-XTGTCCAGACATAGTTYTCTATCYATACG | HIV M184V |
| 94 | HEX-XGACATAGTTATCTYTCAATYCA | 90 No tail |
| 95 | FAM-XGACATAGTTATCTYTCAATYCG | 91 No tail |
| 96 | HEX-XGACATAGTTYTCTATCYATACA | 92 No tail |
| 97 | FAM-XGACATAGTTYTCTATCYATACG | 97 No tail |
| target 112 | 3'- . . . CTGTATCAGTAGATAGTTATGTAC | M184M |

X = iC
Y = iG

Numerous primer combinations were tested including combinations in which each forward primer in the reaction (wild-type and mutant) has 0, 1 or 2 iso-G bases, mismatches at the same, or different positions. Exemplary primer combinations are shown below in Tables 9 and 10.

TABLE 9

| M184M SEQ ID NO: | M184V SEQ ID NO: |
|---|---|
| 80 | 81 |
| (no non-natural bases) | (no non-natural bases) |
| 80 | 87 |
| | (one non-natural base at 27) |
| 80 | 89 |
| | (one non-natural base at 24) |
| 80 | 91 |
| | (two non-natural bases: 21 and 27) |
| 86 | 81 |
| (one non-natural base at base 28) | (no non-natural bases) |
| 86 | 87 |
| | (one non-natural base at 27) |
| 86 | 89 |
| | (one non-natural base at 24) |
| 86 | 91 |
| | (two non-natural bases: 21 and 27) |
| 88 | 81 |
| (one non-natural base at base 25) | (no non-natural bases) |
| 88 | 87 |
| | (one non-natural base at 27) |

TABLE 9-continued

| M184M SEQ ID NO: | M184V SEQ ID NO: |
|---|---|
| 88 | 89 |
| | (one non-natural base 24) |
| 88 | 91 |
| | (two non-natural bases: 21 and 27) |
| 92 | 81 |
| (one non-natural base at base 25) | (no non-natural bases) |
| 92 | 87 |
| | (one non-natural base at 27) |
| 92 | 89 |
| | (one non-natural base 24) |
| 92 | 91 |
| | (two non-natural bases: 21 and 27) |

TABLE 10

| SEQ ID NO: M184M | SEQ ID NO: M184V |
|---|---|
| 84 | 85 |
| (no non-natural bases) | (no non-natural bases) |
| 84 | 89 |
| | (one non-natural base at oligonucleotide position 28) |
| 84 | 95 |
| | (two non-natural base: 21 and 27) |
| 88 | 85 |
| (one non-natural base at 29) | (no non-natural bases) |
| 88 | 89 |
| | (one non-natural base at 28) |
| 88 | 95 |
| | (two non-natural bases: 21 and 27) |
| 96 | 85 |
| (two non-natural bases: 18 and 25) | (no non-natural bases) |
| 96 | 89 |
| | (one non-natural base at 28) |
| 96 | 95 |
| | (two non-natural base: 21 and 27) |

PCR reaction were performed in 1× ISOlution buffer (EraGen Biosciences, Madison, Wis.) containing 100 µM diCTP, 200 nM forward primers, 400 nM reverse primer and 3×10$^4$ linearized plasmid targets. PCR was performed using the ABI 7900 with the following parameters:

2 minute denature at 95° C. followed by 2 cycles of (5 s at 95° C., 30 s at 45° C., 20 s at 72° C.), followed by 70 cycles of (5 s at 95° C., 10 s at 55° C., 20 s at 72° C.), melt 60° C. to 95° C. with 7% gradient.

Figure 5:
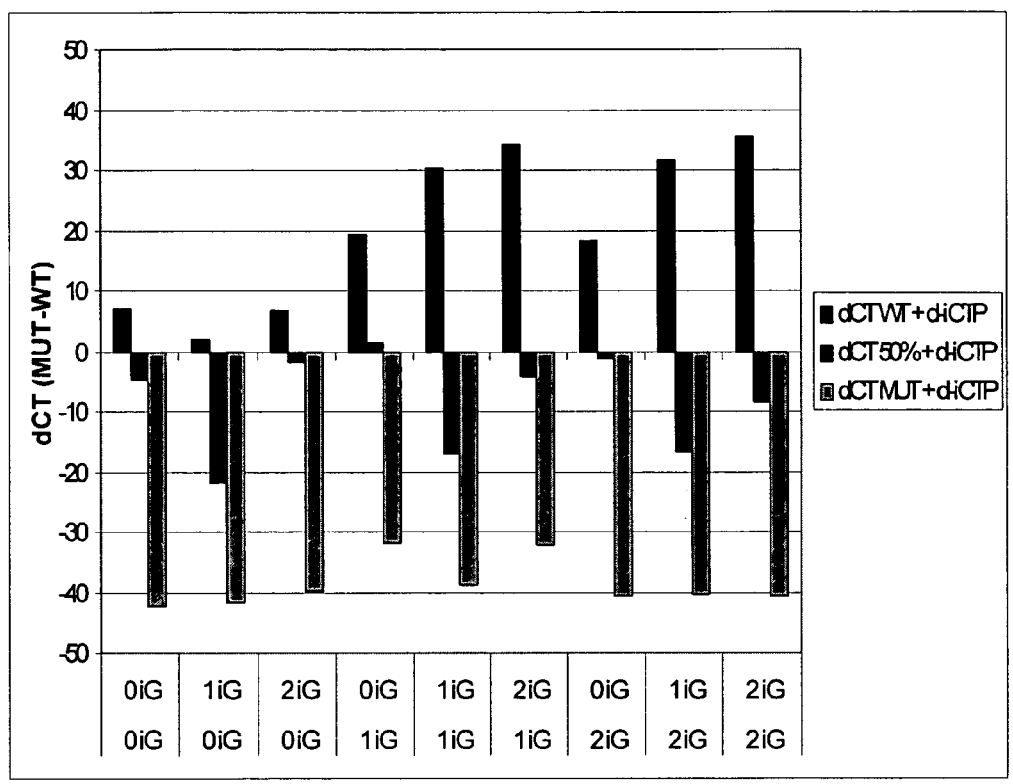
FIGS. 5 and 6 show a $\Delta C_t$ comparison ("dCt") of different mutant and wild-type M184 primer pairs having 0, 1 or 2 iso-Gs in the sequence.
Figure 6:
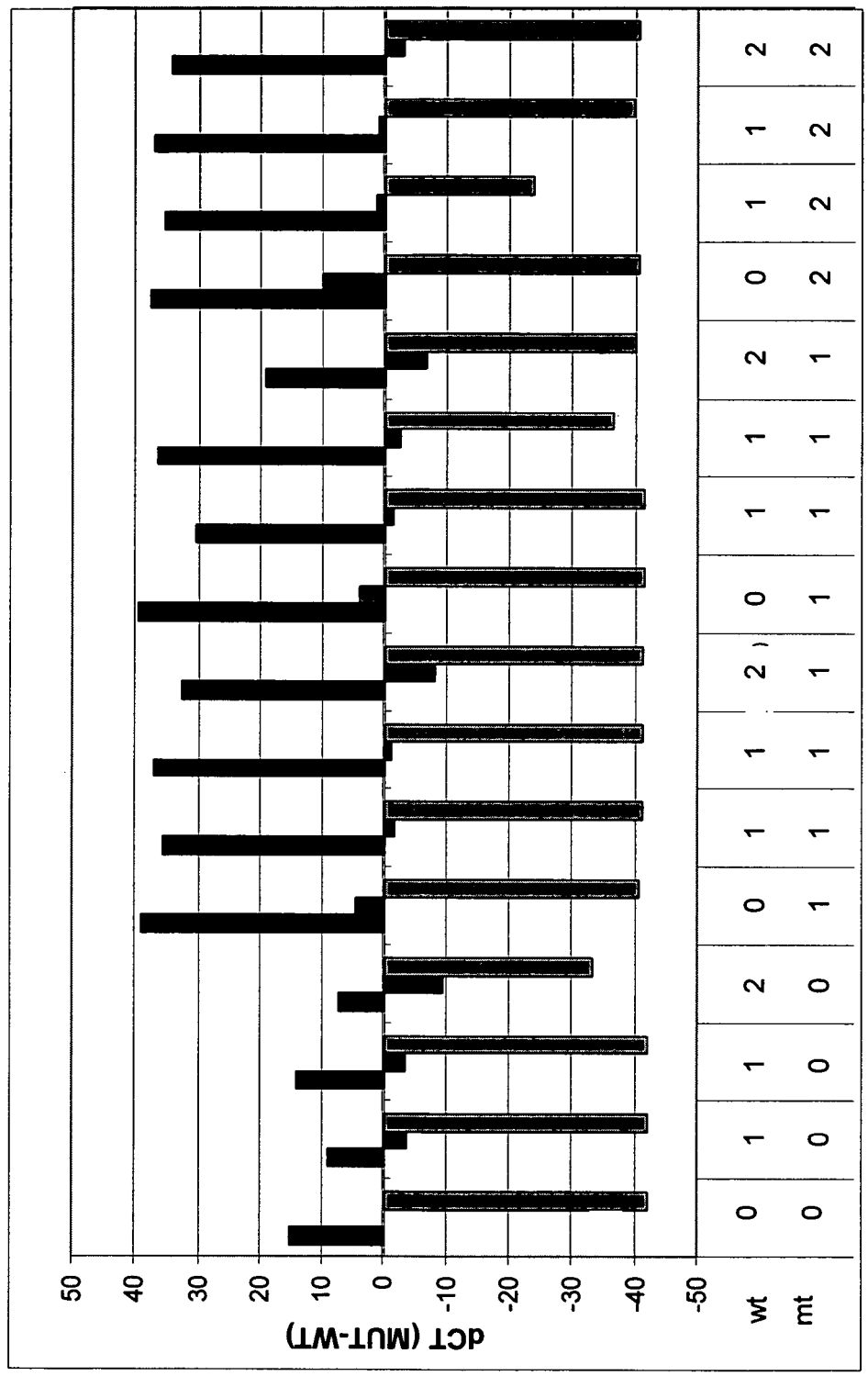

Results indicate that the addition of non-natural mismatches in different positions in the mutant and wild-type primers allows discrimination of mutant and wild-type targets. Data is shown in FIGS. 5 and 6. FIGS. 5 and 6 show the difference in cycle threshold ("dCt") of Mutant Signal minus Wild-Type Signal for different primer pairs. Each set of three bars indicates results using (a) 100% wild-type M184M target (black bars); (b) 50% wild-type M184M and 50% mutant M184V target (dark grey bars in FIG. 5) or 10% mutant target (dark grey bars in FIG. 6); and (c) 100% mutant M184V target (light grey bars).

Note that primer concentration, salt, buffer conditions, temperature, cycling parameters, and enzyme identity may effect dCt values for any of the primer pairs tested.

L. Healing Primers

Figure 7:
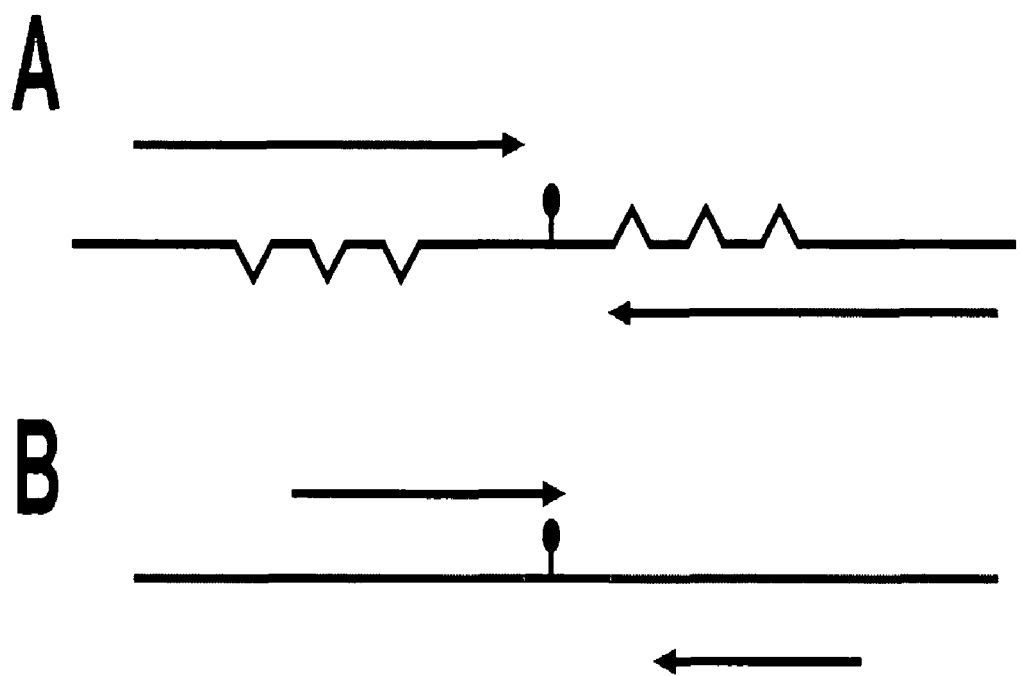
FIG. 7 shows a schematic representation of the "healing primer" strategy.

Another strategy employed to improve genotyping results involved "healing" primers as illustrated in FIG. 7. Part A of FIG. 7 illustrates long primers of high Tm (gray arrows) that can amplify polymorphic HIV-1 despite the presence of mismatches between primer and template. The forward primer terminates just upstream of the target drug-resistance mutation (filled circle). The healing primers may be designed to have a sequence that is highly homologous to the detection primers. Part B shows that the amplification reaction using the healing primers results in a bipartite template that contains perfect matches (gray lines) to the RTx primers which flank the mutation contained within the original HIV-1 genome (black line). The healed HIV-1 target can now be amplified by the primers of the present method (black arrows).

The forward healing primer was designed with a 3' end that terminates just upstream of the drug-resistance mutation site of interest. Since the long healing primers have a higher Tm than that of the detection primers, hybridization and primer extension are expected to occur despite the presence of mismatches between the primer and template. Thus, amplification with the healing primers yields an amplification product from the polymorphic HIV-1 target that matches the detection primer binding sites but still contains the sequence context of the viral template drug-resistance mutation.

Reactions using healing primers were performed on the MJ PTC-200 as follows: a pre-PCR amplification with the healing primers used the following cycling parameters: 2 minutes at 95° C., followed by 40 cycles of 10 s at 95° C., 10 s at 55° C., 20 s at 72° C. Samples were then transferred to the ABI 7900 and the following cycling parameters were used: 2 minutes at 95° C., followed by 1 cycle of 5 s at 95° C., 5 s at 45° C., 20 s at 72° C., followed by 50 cycles of 5 s at 95° C., 5 s at 55° C., 20 s at 72° C., melt 60° C. to 95° C., 2% ramp.

Results using the healing primers and the same set of plasmid cDNA targets described in Table 7 above, are shown in Table 11 below. Black filled columns A-C indicate RTx genotyping reactions where the correct genotype was obtained. Reactions: A, standard RTx primers and 2×10⁶ copies target used. B, healing forward primer combined with, standard RTx primers and on 2×10⁶ copies target DNA; C, 40 rounds healing forward and reverse primer (pre-amplification) with 2×10⁶ copies plasmid DNA. The PCR product was diluted to 2×10⁵ copies for RTx with the standard primers.

As in section H, the standard primers could only genotype 6 of 13 subject-derived clones (Column A). Inclusion of an unlabeled 39 bp healing forward primer with sequence identical to pNL4-3 at 5 nM (and detection primers at 200 nM) allowed 9 of 13 samples to be amplified and genotyped with the initial pNL4-3 standard design (Column B). Finally, pre-amplification of all 13 clones tested with healing forward and reverse primers produced PCR amplification products that could be correctly genotyped by the standard pNL4-3 based RTx primers (Column C).

M. Detection of HIV-1 Mutations from Additional Viral Isolates

Two additional panels of 20 wild-type patient viral RNA isolates were tested (data courtesy of Gilead Sciences). The first panel contained confirmed wild-type K65 isolates, the second panel contained confirmed wild-type M148 isolates. Some of these samples had low viral loads as determined by Amplicor (Amplicor® HIV Monitor, Roche, Indianapolis, Ind.). Additionally, complete population sequences of the target regions were known.

Amplification conditions using the LightCycler were as follows:

2 minutes at 95° C., followed by 3 cycles of 5 s at 95° C., 5 s at 61° C., 1° C./sec, 10 s at 72° C., followed by one cycle of (5 s at 95° C., 5 s at 45° C., 1° C./sec 20 s at 72° C., followed by 110 cycles of 5 s at 95° C., 5 s at 55° C., 20 s at 72° C., melt 60° C. to 95° C. 0.4° C. STEP.

Seventeen of 20 K65 viral RNA samples were successfully amplified using the standard K65 assay design. The failed samples had viral loads ranging from 3,900 to <400 copies per mL. The three samples that failed to amplify with standard primer designs had viral loads ranging from 3900 to less than 400 copies per mL. All 17 genotypes were determined to be 100% K65K (wild-type).

Sixteen of 20 M184 viral RNA samples were successfully amplified using the standard M184 assay design. By including a forward healing primer into the M184V reactions as described above, 19 of 20 samples were genotyped. The sample that failed had a very low viral load of <400 copies per mL. Additionally, all of the sample K65 and M184 genotype results were correct, that is, seventeen of seventeen K65 and nineteen of nineteen M184 results were found to be 100% concordant with the previously determined genotypes.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

TABLE 11

|  | Reaction | | |
| --- | --- | --- | --- |
| Sample | A | B | C |
| pNL4-3 | ■ | ■ | ■ |
| 7324-1 |  | ■ | ■ |
| 7324-4 |  | ■ | ■ |
| 10076-4 | ■ | ■ | ■ |
| 7295-1 |  |  | ■ |
| 4755-1 |  | ■ | ■ |
| 6463-13 | ■ | ■ | ■ |
| 7303-3 |  | ■ | ■ |
| 1617-1 |  | ■ | ■ |
| 35764-2 | ■ | ■ | ■ |
| 29129-2 | ■ |  | ■ |
| 52534-2 | ■ | ■ | ■ |
| 56252-1 |  |  | ■ |
| 12-21 |  | ■ | ■ |

All references, patents, and/or applications cited in the specification are incorporated by reference in their entireties, including any tables and figures, to the same extent as if each reference had been incorporated by reference in its entirety individually.

---

What is claimed is:

1. A method for detecting a specific mutation in a heterogeneous population of polynucleotides, wherein the specific mutation, if present, is located in a first region of the polynucleotides of the population, the method comprising:
   (a) amplifying the polynucleotides of the population with a first set of primers to obtain an amplification product that comprises the first region, wherein at least one primer of the first set of primers is a healing primer that specifically hybridizes to a region of the heterogeneous population of polynucleotides that comprises one or more additional mutations, and none of the primers of the first set of primers hybridizes to the first region; and
   (b) amplifying the amplification product with a second set of primers to detect the specific mutation, wherein the second set of primers comprises a first primer having a nucleotide that is complementary to the first region if the specific mutation is present and the first primer includes at least one non-natural base selected from iso-G or iso-C, and further wherein one or more of the primers of the second set of primers comprises a label.

2. The method of claim 1, wherein the second set of primers further comprises a second primer having a nucleotide that is complementary to the first region if the mutation is absent and the second primer includes at least one non-natural base selected from iso-G or iso-C.

3. The method of claim 2, wherein the first and second primers of the second primer set each include a label and the label is a fluorophore.

4. The method of claim 3, wherein the first and second primers of the second primer set include different fluorophores.

5. The method of claim 4, wherein the amplification product is amplified in a reaction mixture that includes a non-natural nucleotide that is capable of base-pairing with the non-natural base of the first and second primers and is coupled to a quencher that is capable of quenching the different fluorophores.

6. The method of claim 1, wherein the first primer of the second set of primers is fully complementary to the first region if the specific mutation is present, other than at the non-natural base of the first primer.

7. The method of claim 1, wherein the specific mutation comprises a single base change.

8. The method of claim 1, wherein the first region consists of a single nucleotide.

9. The method of claim 1, wherein at least one primer of the first set of primers includes at least one non-natural base selected from iso-G or iso-C.

10. The method of claim 1, wherein the population of polynucleotides comprises a nucleic acid sequence of HIV-1.

11. The method of claim 1, wherein the first primer of the second set of primers has a 3' nucleotide or a nucleotide within 1 or 2 bases of the 3' nucleotide that is complementary to the first region if the specific mutation is present.

12. The method of claim 1, wherein the second set of primers comprises a second primer having a 3' nucleotide or a nucleotide within 1 or 2 bases of the 3' nucleotide that is complementary to the first region if the mutation is absent.

13. A method of detecting the presence or absence of a mutation at a specific nucleotide position in a polynucleotide from a sample, comprising amplifying the polynucleotide with primers to detect the presence or absence of the mutation in the polynucleotide, the primers comprising:
   (a) a first primer that is complementary to the polynucleotide at the specific nucleotide position of the mutation if the mutation is present in the polynucleotide;
   (b) a second primer that is complementary to the polynucleotide at the specific nucleotide position of the mutation if the mutation is absent in the polynucleotide;
   wherein the first primer and the second primer include a non-natural base selected from iso-G or iso-C at one or more positions other than the specific nucleotide position of the mutation to create one or more non-adjacent mismatches across from a target base in a target specific sequence of the first primer and the second primer, and at least one of the first primer and the second primer includes a label.

14. The method of claim 13, wherein the first primer has a 3' nucleotide or a nucleotide within 1 or 2 bases of the 3' nucleotide that is complementary to the polynucleotide at the specific nucleotide position of the mutation if the mutation is present in the polynucleotide.

15. The method of claim 13, wherein the second primer has a 3' nucleotide or a nucleotide within 1 or 2 bases of the 3' nucleotide that is complementary to the polynucleotide at the specific nucleotide position of the mutation if the mutation is absent in the polynucleotide.

16. The method of claim 13, wherein the first primer and the second primer are not complementary to the polynucleotide at a single position other than the specific position of the mutation and do not include identical nucleotides at the single position.

17. The method of claim 13, wherein the label comprises a fluorophore.

18. The method of claim 17, wherein the amplification is performed in a reaction mixture that includes a non-natural nucleotide that is capable of base-pairing with the non-natural base of the first and second primers and is coupled to a quencher that is capable of quenching the fluorophores.

19. The method of claim 13, wherein the primers are capable of specifically hybridizing to an HIV-1 polynucleotide, thereby detecting the presence or absence of an HIV-1 mutation in the sample.

20. The method of claim 13, further comprising the step of quantitating the amount of polynucleotides in the sample where the mutation is present or absent by measuring the amount of amplification products amplified by the first primer, the second primer, or both.

21. The method of claim 20, wherein the relative amount of polynucleotides where the mutation is present compared to the polynucleotides where the mutation is absent in the sample is determined.

22. The method of claim 21, wherein the sample comprises no more than about 1% of polynucleotides where the mutation is present relative to polynucleotides where the mutation is absent.

23. The method of claim 21, wherein the sample comprises no more than about 0.1% of polynucleotides where the mutation is present relative to polynucleotides where the mutation is absent.

24. A method of detecting the presence or absence of a mutation at a specific nucleotide position in a polynucleotide from a sample, comprising: amplifying the polynucleotide with primers to detect the presence or absence of the mutation in the polynucleotide, the primers comprising:
  (a) a first primer comprising:
    (i) a mutation-specific region comprising a single nucleotide, wherein the sequence of the mutation-specific region is complementary to the polynucleotide at the specific nucleotide position of the mutation if the mutation is present in the polynucleotide;
    (ii) a target specific region, wherein the target specific region hybridizes to the polynucleotide at a position adjacent to the specific nucleotide position of the mutation, and wherein the target specific region includes a non-natural base selected from iso-C or iso-G at one or more positions;
  (b) a second primer comprising:
    (i) a mutation-specific region comprising a single nucleotide, wherein the sequence of the mutation-specific region is complementary to the polynucleotide at the specific nucleotide position of the mutation if the mutation is absent in the polynucleotide;
    (ii) a target specific region, wherein the target specific region hybridizes to the polynucleotide at a position adjacent to the specific nucleotide position of the mutation, and wherein the target specific region includes a non-natural base selected from iso-C or iso-G at one or more positions;
  wherein at least one of the first primer and the second primer includes a label.

* * * * *

UNITED STATES PATENT AND TRADEMARK OFFICE
CERTIFICATE OF CORRECTION

| | | |
|---|---|---|
| PATENT NO. | : 8,293,472 B2 | Page 1 of 1 |
| APPLICATION NO. | : 11/447734 | |
| DATED | : October 23, 2012 | |
| INVENTOR(S) | : Michael James Moser | |

It is certified that error appears in the above-identified patent and that said Letters Patent is hereby corrected as shown below:

On the title page, item (57) Abstract, line 5, delete "cause" and insert --causing-- therefor.

Signed and Sealed this
Eleventh Day of December, 2012

David J. Kappos
*Director of the United States Patent and Trademark Office*

SEQUENCE LISTING

<160> NUMBER OF SEQ ID NOS: 112

<210> SEQ ID NO 1
<211> LENGTH: 1003
<212> TYPE: PRT
<213> ORGANISM: Human immunodeficiency virus type 1

<400> SEQUENCE: 1

```
Phe Phe Arg Glu Asp Leu Ala Phe Pro Gln Gly Lys Ala Arg Glu Phe
  1               5                  10                  15

Ser Ser Glu Gln Thr Arg Ala Asn Ser Pro Thr Arg Arg Glu Leu Gln
             20                  25                  30

Val Trp Gly Arg Asp Asn Asn Ser Leu Ser Glu Ala Gly Ala Asp Arg
         35                  40                  45

Gln Gly Thr Val Ser Phe Ser Phe Pro Gln Ile Thr Leu Trp Gln Arg
     50                  55                  60

Pro Leu Val Thr Ile Lys Ile Gly Gly Gln Leu Lys Glu Ala Leu Leu
 65                  70                  75                  80

Asp Thr Gly Ala Asp Asp Thr Val Leu Glu Glu Met Asn Leu Pro Gly
                 85                  90                  95

Arg Trp Lys Pro Lys Met Ile Gly Gly Ile Gly Gly Phe Ile Lys Val
            100                 105                 110

Gly Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240

Asp Phe Trp Glu Val Gln Leu Gly Ile Pro His Pro Ala Gly Leu Lys
                245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
        275                 280                 285

Ser Ile Asn Asn Glu Thr Pro Gly Ile Arg Tyr Gln Tyr Asn Val Leu
    290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Ile Val Ile Tyr
```

```
                    325                 330                 335
Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
        355                 360                 365

Phe Thr Thr Pro Asp Lys Lys His Gln Lys Glu Pro Pro Phe Leu Trp
    370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
                405                 410                 415

Gly Lys Leu Asn Trp Ala Ser Gln Ile Tyr Ala Gly Ile Lys Val Arg
            420                 425                 430

Gln Leu Cys Lys Leu Leu Arg Gly Thr Lys Ala Leu Thr Glu Val Val
        435                 440                 445

Pro Leu Thr Glu Glu Ala Glu Leu Glu Leu Ala Glu Asn Arg Glu Ile
    450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
                485                 490                 495

Tyr Gln Glu Pro Phe Lys Asn Leu Lys Thr Gly Lys Tyr Ala Arg Met
            500                 505                 510

Lys Gly Ala His Thr Asn Asp Val Lys Gln Leu Thr Glu Ala Val Gln
        515                 520                 525

Lys Ile Ala Thr Glu Ser Ile Val Ile Trp Gly Lys Thr Pro Lys Phe
    530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
                565                 570                 575

Leu Val Lys Leu Trp Tyr Gln Leu Glu Lys Glu Pro Ile Ile Gly Ala
            580                 585                 590

Glu Thr Phe Tyr Val Asp Gly Ala Ala Asn Arg Glu Thr Lys Leu Gly
        595                 600                 605

Lys Ala Gly Tyr Val Thr Asp Arg Gly Arg Gln Lys Val Val Pro Leu
    610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
    690                 695                 700

Gly Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750
```

-continued

```
Ala Ser Cys Asp Lys Cys Gln Leu Lys Gly Glu Ala Met His Gly Gln
        755                 760                 765
Val Asp Cys Ser Pro Gly Ile Trp Gln Leu Asp Cys Thr His Leu Glu
    770                 775                 780
Gly Lys Val Ile Leu Val Ala Val His Val Ala Ser Gly Tyr Ile Glu
785                 790                 795                 800
Ala Glu Val Ile Pro Ala Glu Thr Gly Gln Glu Thr Ala Tyr Phe Leu
                805                 810                 815
Leu Lys Leu Ala Gly Arg Trp Pro Val Lys Thr Val His Thr Asp Asn
            820                 825                 830
Gly Ser Asn Phe Thr Ser Thr Val Lys Ala Ala Cys Trp Trp Ala
        835                 840                 845
Gly Ile Lys Gln Glu Phe Gly Ile Pro Tyr Asn Pro Gln Ser Gln Gly
    850                 855                 860
Val Ile Glu Ser Met Asn Lys Glu Leu Lys Lys Ile Ile Gly Gln Val
865                 870                 875                 880
Arg Asp Gln Ala Glu His Leu Lys Thr Ala Val Gln Met Ala Val Phe
                885                 890                 895
Ile His Asn Phe Lys Arg Lys Gly Gly Ile Gly Gly Tyr Ser Ala Gly
            900                 905                 910
Glu Arg Ile Val Asp Ile Ile Ala Thr Asp Ile Gln Thr Lys Glu Leu
        915                 920                 925
Gln Lys Gln Ile Thr Lys Ile Gln Asn Phe Arg Val Tyr Tyr Arg Asp
    930                 935                 940
Ser Arg Asp Pro Val Trp Lys Gly Pro Ala Lys Leu Leu Trp Lys Gly
945                 950                 955                 960
Glu Gly Ala Val Val Ile Gln Asp Asn Ser Asp Ile Lys Val Val Pro
                965                 970                 975
Arg Arg Lys Ala Lys Ile Ile Arg Asp Tyr Gly Lys Gln Met Ala Gly
            980                 985                 990
Asp Asp Cys Val Ala Ser Arg Gln Asp Glu Asp
        995                 1000

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcagatttc tatgagtatc tgat                                            24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 3
ngtttagcat acaggagcag atg                                             23

<210> SEQ ID NO 4
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 4
nggcatgata caggagcaga ta                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttccaatta tgttgacagg tg                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 6
ngagcgatgg aaaccaaaaa tg                                              22

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 7
ncctgacata gatggaaacc aaaaata                                         27

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cttccaatta tgttgacagg tg                                              22

<210> SEQ ID NO 9
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 9
ngtatcaacg aaaccaaaaa tgatagg                                           27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 10
ncgtcctgaa accaaaaatg atagt                                             25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cttccaatta tgttgacagg tg                                                22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 12
nactgatgaa atgatagggg gag                                               23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 13
nactgctaaa atgatagggg gaa                                               23

<210> SEQ ID NO 14
<211> LENGTH: 30
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 14
gtacaaattt ctactaatgc ttttatttt                                    30

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 15
ncgacaataa aattggaaga aatctgt                                      27

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 16
ncgccataat tggaagaaat ctga                                         24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaaatactg gagtattgta tgga                                         24

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 18
nccatttact gtagaaattt gtacagaaa                                    29

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (1)
<223> OTHER INFORMATION: iso-c

<400> SEQUENCE: 19
nggctggtag aaatttgtac agaat                                              25

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcaaatactg gagtattgta tgga                                               24

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 21
nccatttact gtagaaattt gtacagaaa                                          29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 22
nggtaaatga gtagaaattt gtacagaac                                          29

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attcctaatt gaacttccca gaaa                                               24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (1)
<223> OTHER INFORMATION: iso-c

<400> SEQUENCE: 24
ncttgctcag aaatggaaaa ggaa                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 25
nctggatgag aaatggaaaa ggac                                          24

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctcaacagat gttgtctcag ttcctcta                                      28

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 27
ngacaggaga catagtcatc tatcaataca                                    30

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 28
ntgtccaata gtcatctatc aatacg                                        26

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 29
taaatcccca cctcaacaga t                                              21

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 30
ngagtaagct agtcatctat caatacatg                                      29

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 31
ncagccatag tcatctatca atacg                                          25

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaaaaatatg catcgcccac                                                20

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 33
ntcgctcata aagaaaaaag acagta                                         26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
```

<400> SEQUENCE: 34
ncggttcata aagaaaaaag acagtc                               26

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catcgcccac atccag                                          16

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 36
ngctacgagt actaaatgga gaaaat                               26

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 37
nccctgtgta ctaaatggag aaaag                                25

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccctggtgtc tcattgttt                                       19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 39
ntgttgaaat cctgcagggt                    20

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 40
nagacgatcc tgcaggga                    18

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ccctggtgtc tcattgttt                    19

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 42
naggacccag ggttaaaaca gaaa                    24

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 43
ngtctcgagg gttaaaacag aac                    23

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tgtcatgcta cactggaata ttg                    23

```
<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 45
ntgcccgatg catattttc ag                                              22

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 46
ntccgtcgat gcatattttt caa                                            23

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
taaatcccca cctcaacaga t                                              21

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 48
nccgttccag acatagtcat cta                                            23

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 49
naggcacaga catagtcatc tg                                             22
```

```
<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
taaatcccca cctcaacaga t                                              21

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 51
nccgttccag acatagtcat cta                                            23

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 52
nggttagtcc agacatagtc atca                                           24

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
taaatcccca cctcaacaga t                                              21

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 54
ngagtaagct agtcatctat caatacatg                                      29

<210> SEQ ID NO 55
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 55
ncattcgcat agtcatctat caatacata                                    29

<210> SEQ ID NO 56
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
accctgcagg atgtgg                                                  16

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 57
nacaggtagt atttgccata aagaa                                        25

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 58
ngacatcgta tttgccataa agag                                         24

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctgatttttt ctgttttaac cctgc                                        25

<210> SEQ ID NO 60
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 60
ntcacgtagt atttgccata aagaa                                           25

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 61
ntgctggtat ttgccataaa gag                                             23

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aaggaatgga ggttctttct g                                               21

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 63
ngacggtaat acatggatga tttgta                                          26

<210> SEQ ID NO 64
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 64
ngcctaagac atggatgatt tgc                                             23

<210> SEQ ID NO 65
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 65
aaggaatgga ggttctttct g                                              21

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 66
ngacggtaat acatggatga tttgta                                         26

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 67
nccgctatac atggatgatt tgtt                                           24

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
agcactatag gctgtactgt c                                              21

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 69
natctgtttg aggtggggat tta                                            23

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<220> FEATURE:
<221> NAME/KEY: modified_base
<222> LOCATION: (1)
<223> OTHER INFORMATION: iso-c

<400> SEQUENCE: 70
ntgtgagagg tgggatttt t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
agcactatag gctgtactgt c                                             21

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 72
natctgtttg aggtggggat tta                                           23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 73
nctagacaga ggtggggatt tta                                           23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gacatrgtya tctatcarta yr                                            22

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
```
gacatagtca tctatcaata cr                                        22

<210> SEQ ID NO 76
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 76
ngacaggaga catagttatc tatcaatata                                30

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 77
ntgtccagac atagttatct atcaatagg                                 29

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 78
ngacaggaga catagttatc tatcaataca                                30

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 79
ntgtccagac atagttatct atcaatacg                                 29

<210> SEQ ID NO 80
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (1)
<223> OTHER INFORMATION: iso-c

<400> SEQUENCE: 80
ngacaggaga catagttatc tatcaataca                                    30

<210> SEQ ID NO 81
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c

<400> SEQUENCE: 81
ntgtccagac atagttatct atcaatacg                                     29

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (29)
<223> OTHER INFORMATION: iso-c

<400> SEQUENCE: 82
ngacaggaga catagttatc tatcaatana                                    30

<210> SEQ ID NO 83
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (28)
<223> OTHER INFORMATION: iso-c

<400> SEQUENCE: 83
ntgtccagac atagttatct atcaatang                                     29

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
```

```
<222> LOCATION: (29)
<223> OTHER INFORMATION: iso-g

<400> SEQUENCE: 84
ngacaggaga catagttatc tatcaatana                                              30

<210> SEQ ID NO 85
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (28)
<223> OTHER INFORMATION: iso-g

<400> SEQUENCE: 85
ntgtccagac atagttatct atcaatang                                               29

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (28)
<223> OTHER INFORMATION: iso-g

<400> SEQUENCE: 86
ngacaggaga catagttatc tatcaatnca                                              30

<210> SEQ ID NO 87
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (27)
<223> OTHER INFORMATION: iso-g

<400> SEQUENCE: 87
ntgtccagac atagttatct atcaatncg                                               29

<210> SEQ ID NO 88
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
```

```
<222> LOCATION: (1)
<223> OTHER INFORMATION: iso-c
<220> FEATURE:
<221> NAME/KEY: modified_base
<222> LOCATION: (25)
<223> OTHER INFORMATION: iso-g

<400> SEQUENCE: 88
ngacaggaga catagttatc tatcnataca                                          30

<210> SEQ ID NO 89
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (24)
<223> OTHER INFORMATION: iso-g

<400> SEQUENCE: 89
ntgtccagac atagttatct atcnatacg                                           29

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (22)
<223> OTHER INFORMATION: iso-g
<220> FEATURE:
<221> NAME/KEY: modified_base
<222> LOCATION: (28)
<223> OTHER INFORMATION: iso-g

<400> SEQUENCE: 90
ngacaggaga catagttatc tntcaatnca                                          30

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (21)
<223> OTHER INFORMATION: iso-g
<220> FEATURE:
<221> NAME/KEY: modified_base
<222> LOCATION: (27)
<223> OTHER INFORMATION: iso-g

<400> SEQUENCE: 91
```
ntgtccagac atagttatct ntcaatncg          29

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (18)
<223> OTHER INFORMATION: iso-g
<220> FEATURE:
<221> NAME/KEY: modified_base
<222> LOCATION: (25)
<223> OTHER INFORMATION: iso-g

<400> SEQUENCE: 92
ngacaggaga catagttntc tatcnataca          30

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (17)
<223> OTHER INFORMATION: iso-g
<220> FEATURE:
<221> NAME/KEY: modified_base
<222> LOCATION: (24)
<223> OTHER INFORMATION: iso-g

<400> SEQUENCE: 93
ntgtccagac atagttntct atcnatacg          29

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (15)
<223> OTHER INFORMATION: iso-g
<220> FEATURE:
<221> NAME/KEY: modified_base
<222> LOCATION: (21)
<223> OTHER INFORMATION: iso-g

<400> SEQUENCE: 94
ngacatagtt atctntcaat nca          23

<210> SEQ ID NO 95
<211> LENGTH: 23

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (15)
<223> OTHER INFORMATION: iso-g
<220> FEATURE:
<221> NAME/KEY: modified_base
<222> LOCATION: (21)
<223> OTHER INFORMATION: iso-g

<400> SEQUENCE: 95
ngacatagtt atctntcaat ncg                                         23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (11)
<223> OTHER INFORMATION: iso-g
<220> FEATURE:
<221> NAME/KEY: modified_base
<222> LOCATION: (18)
<223> OTHER INFORMATION: iso-g

<400> SEQUENCE: 96
ngacatagtt ntctatcnat aca                                         23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)
<223> OTHER INFORMATION: iso-c
<220> FEATURE:
<221> NAME/KEY: modified_base
<222> LOCATION: (11)
<223> OTHER INFORMATION: iso-g
<220> FEATURE:
<221> NAME/KEY: modified_base
<222> LOCATION: (18)
<223> OTHER INFORMATION: iso-g

<400> SEQUENCE: 97
ngacatagtt ntctatcnat acg                                         23

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 98
gacatagtca tctatcaata ca                                              22

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gaaatagtta tctatcaata ta                                              22

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gaaatagtta tctatcaata ta                                              22

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gaaatggtta tctatcaata cg                                              22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gacatagtca tctatcaata cg                                              22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gacatagtta tctatcaata tg                                              22

<210> SEQ ID NO 104
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
```

-continued gaaatagtta tctatcaata cg				22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gacatagtta tctatcaata ca				22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gacatggtta tctatcaata tg				22

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gacatagtta tctatcaata ca				22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gatatagtca tctatcaata cg				22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gacatagtta tctatcaata cg				22

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gacatagtta tctatcaata ca				22

```
<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gacatagtta tttaccaata ca                                          22

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
catgtattga tagatgacta tgtc                                        24
```